(12) United States Patent
Wang et al.

(10) Patent No.: US 9,784,710 B2
(45) Date of Patent: Oct. 10, 2017

(54) BIPOLAR ELECTRODE SAMPLE PREPARATION DEVICES

(71) Applicant: CFD Research Corporation, Huntsville, AL (US)

(72) Inventors: Yi Wang, Madison, AL (US); Hongjun Song, Madison, AL (US); Kapil Pant, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 515 days.

(21) Appl. No.: 14/202,105

(22) Filed: Mar. 10, 2014

(65) Prior Publication Data

US 2014/0251813 A1 Sep. 11, 2014

Related U.S. Application Data

(60) Provisional application No. 61/775,205, filed on Mar. 8, 2013.

(51) Int. Cl.
*G01N 27/447* (2006.01)
*B01L 3/00* (2006.01)
(Continued)

(52) U.S. Cl.
CPC .. *G01N 27/44769* (2013.01); *B01L 3/502753* (2013.01); *B01L 3/502761* (2013.01);
(Continued)

(58) Field of Classification Search
CPC ... B01L 2400/0415; B03C 5/026; C07K 1/24; G01N 15/0266; G01N 2001/4038;
(Continued)

(56) References Cited

U.S. PATENT DOCUMENTS 4,032,426 A * 6/1977 de Nora ............. C02F 1/46109
 204/268
5,009,763 A * 4/1991 Hise ...................... F01N 3/0892
 204/255

(Continued)

OTHER PUBLICATIONS

Anand et al. Anal. Chem. Sep. 2010 82,8766-8774.*

(Continued)

*Primary Examiner* — Jill Warden
*Assistant Examiner* — Matthew Krcha
(74) *Attorney, Agent, or Firm* — Maschoff Brennan

(57) ABSTRACT

An analyte selection device can include: a body defining a fluid channel having a channel inlet and channel outlet; a bipolar electrode (BPE) between the inlet and outlet; one of an anode or cathode electrically coupled with the BPE on a channel inlet side of the BPE and the other of the anode or cathode electrically coupled with the BPE on a channel outlet side of the BPE; and an electronic system operably coupled with the anode and cathode so as to polarize the BPE. The fluid channel can have any shape or dimension. The channel inlet and channel outlet can be longitudinal or lateral with respect to the longitudinal axis of the channel. The BPE can be any metallic member, such as a flat plate on a wall or mesh as a barrier BPE. The anode and cathode can be located at a position that polarizes the BPE.

15 Claims, 11 Drawing Sheets

(51) Int. Cl.
  *G01N 15/02* (2006.01)
  *G01N 30/00* (2006.01)
  *B03C 5/02* (2006.01)
  *C07K 1/24* (2006.01)
  *G01N 1/40* (2006.01)

(52) U.S. Cl.
  CPC ......... *B03C 5/026* (2013.01); *G01N 15/0266* (2013.01); *G01N 30/0005* (2013.01); *B01L 2200/0636* (2013.01); *B01L 2200/0652* (2013.01); *B01L 2300/0864* (2013.01); *B01L 2400/0415* (2013.01); *B01L 2400/0487* (2013.01); *B03C 2201/26* (2013.01); *C07K 1/24* (2013.01); *G01N 2001/4038* (2013.01); *G01N 2015/0288* (2013.01); *G01N 2030/0065* (2013.01)

(58) Field of Classification Search
  CPC ... G01N 2015/0288; G01N 2030/0065; G01N 27/44769; G01N 30/0005
  See application file for complete search history.

(56) References Cited

U.S. PATENT DOCUMENTS 5,419,824 A * 5/1995 Weres ................. C02F 1/46109
                                                   204/242
2004/0129579 A1 * 7/2004 Crooks ................. C12Q 1/001
                                                   205/775

OTHER PUBLICATIONS

Robbyn K. Perdue, Derek R. Laws, Dzmitry Hlushkou, Ulrich Tallarek, and Richard M. Crooks, Bipolar Electrode Focusing: The Effect of Current and Electric Field on Concentration Enrichment, Dec. 15, 2009, 7 pages, vol. 81, No. 24.

Robbyn K. Anand, Derek R. Laws, Kwok-Fan Chow, Byoung-Young Chang, John A. Crooks, and Richard M. Crooks, Bipolar Electrodes: A Useful Tool for Concentration, Separation, and Detection of Analytes in Microelectrochemical Systems, Sep. 3, 2010, 9 pages, vol. 82, No. 21.

* cited by examiner

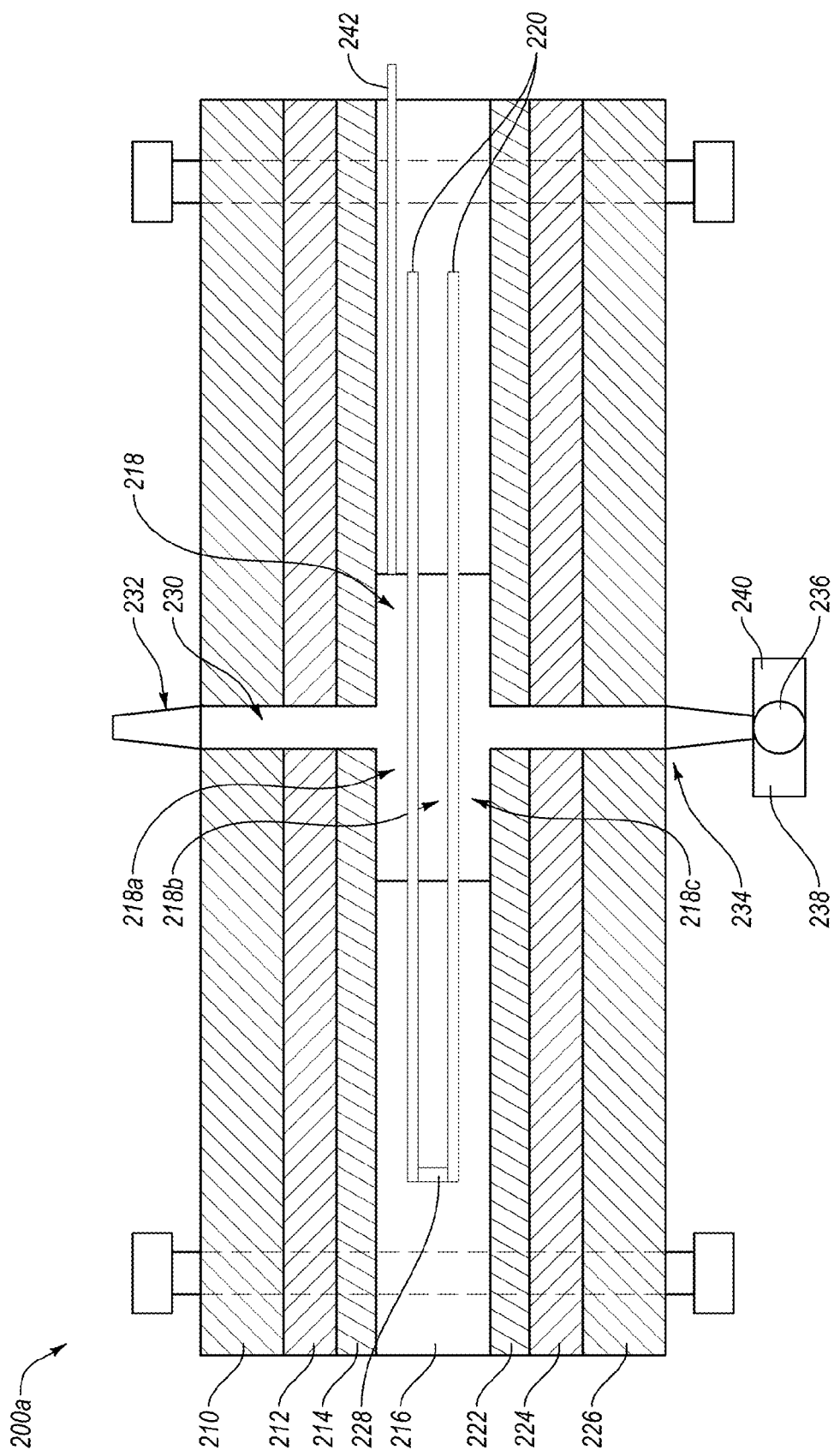

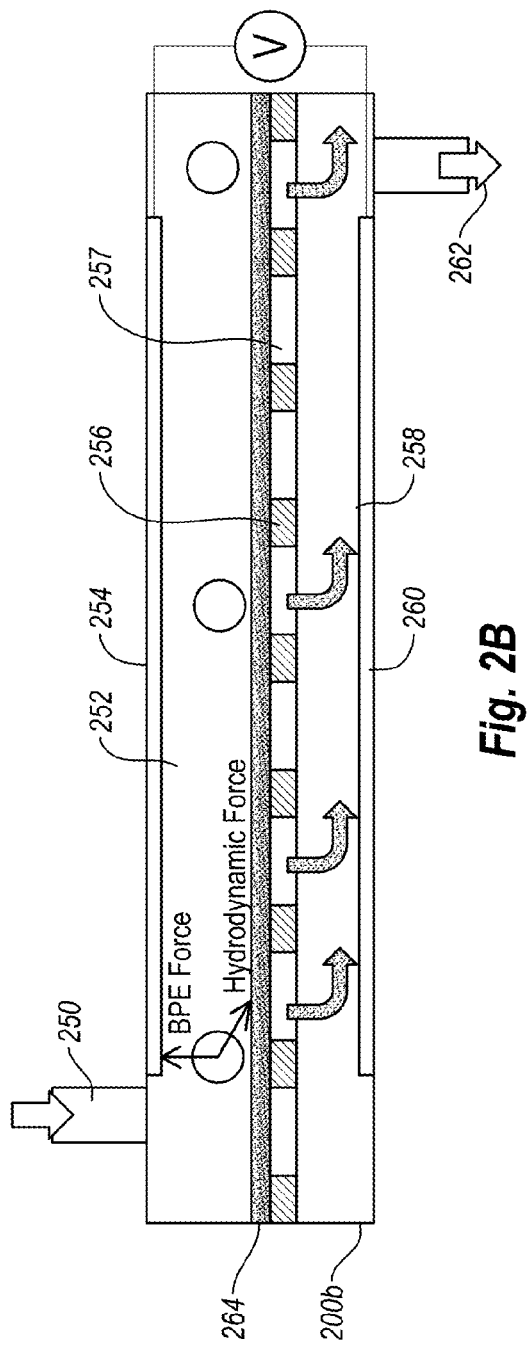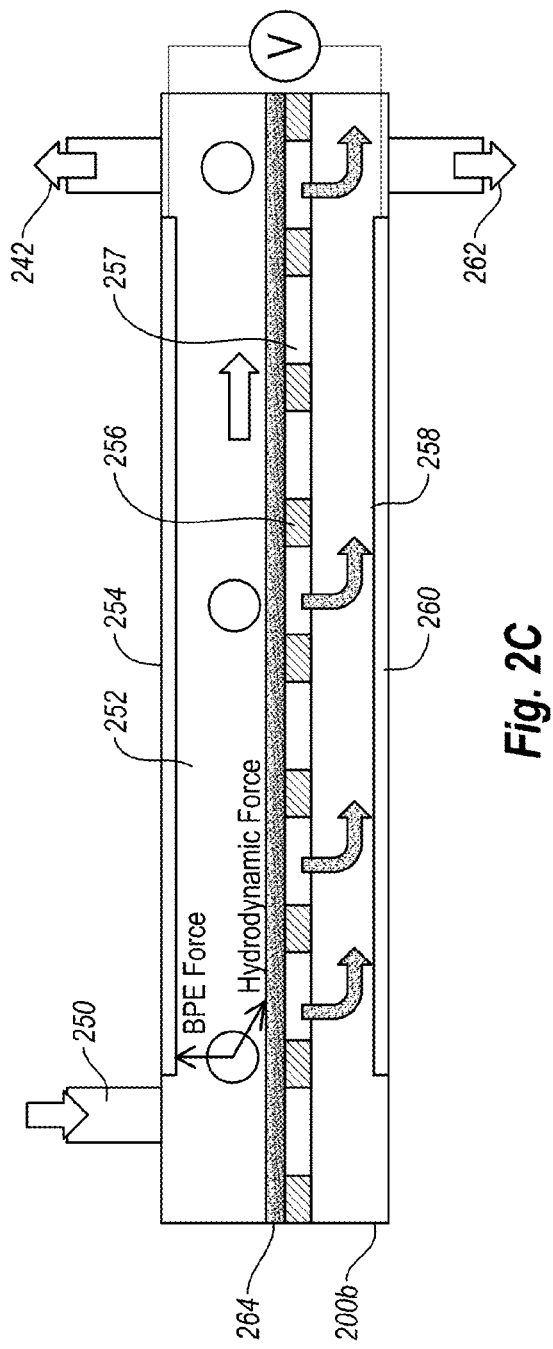
Fig. 2B
Fig. 2C

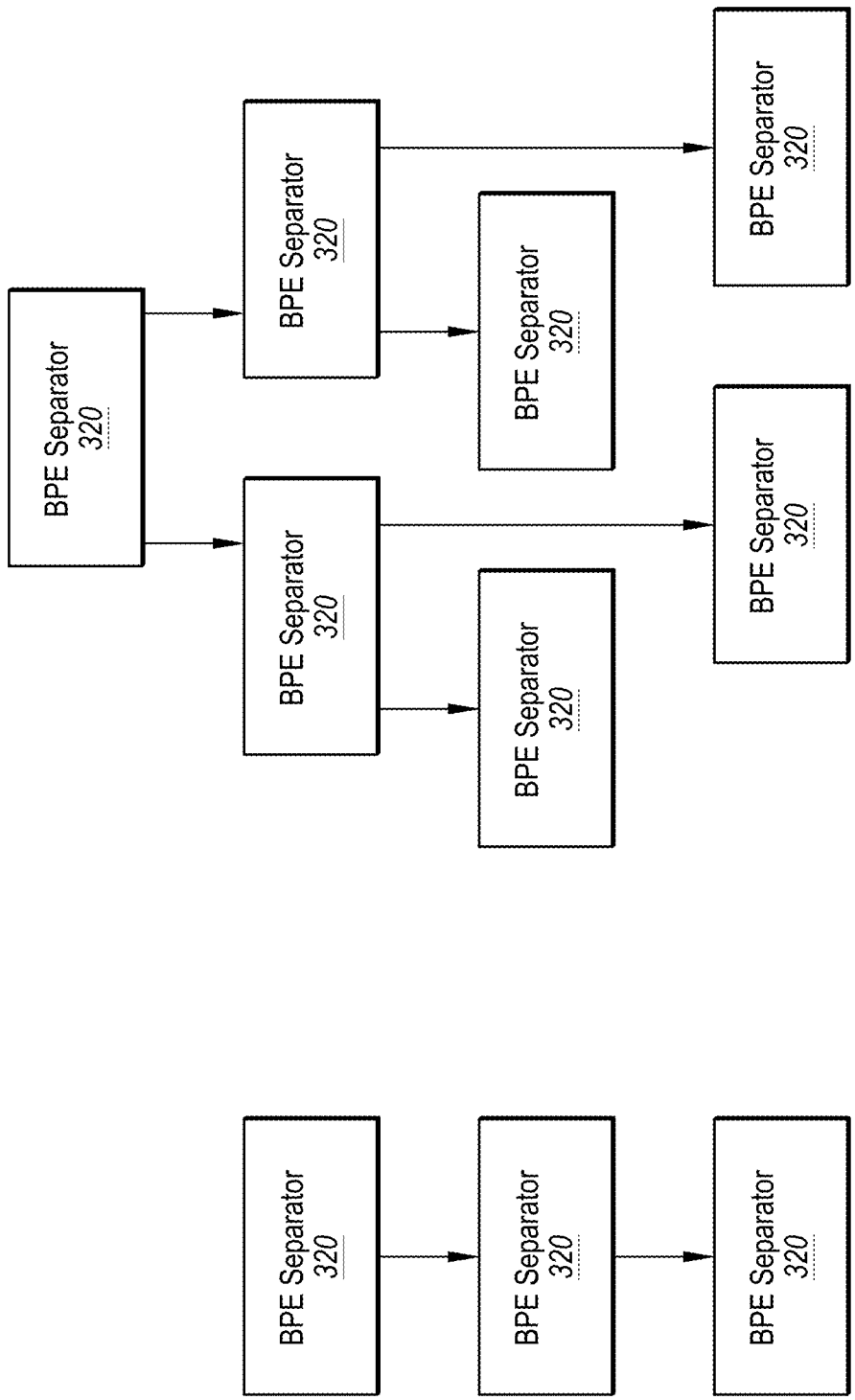

BIPOLAR ELECTRODE SAMPLE PREPARATION DEVICES

CROSS-REFERENCE

This patent application claims priority to U.S. Provisional Application No. 61/775,205 filed Mar. 8, 2013, which provisional application is incorporated herein by specific reference in its entirety.

GOVERNMENT SUPPORT

This invention was made with government support under NNX11CC08C awarded by NASA and under 5R44HG004290-03 awarded by the NIH. The government has certain rights in the invention.

BACKGROUND

Advancing technologies often rely on concentrated or purified materials. As such, there continues to be a need to improve concentration and purification devices and methods. Commonly used purification methods for recovering and purifying protein include: Ion-exchange chromatography separates proteins with differences in charge and has high sample loading capacity. The separation is based on the reversible interaction between a charged protein and an oppositely charged chromatographic medium; Size-exclusion chromatography is a separation technique based on the molecular size of the components. Separation is achieved by the differential exclusion from the pores of the packing material, of the sample molecules as they pass through a bed of porous particles; hydrophobic interaction chromatography separates proteins with differences in hydrophobicity. The separation is based on the reversible interaction between a protein and the hydrophobic surface of a chromatographic medium; affinity chromatography separates molecules based on the reversible interaction between target protein and the specific ligand attached to a chromatography matrix; aqueous phase separation is an aqueous, liquid-liquid, biphasic system which is obtained either by mixture of aqueous solution of two polymers, or a polymer and a salt. Generally, the former aqueous is comprised of PEG and polymers like dextran, starch, polyvinylalcohol, etc. The latter one is composed of PEG and phosphate or sulphate salts; and self-cleaving affinity tag with low-cost resin combine self-cleaving affinity tag with the low-cost affinity resin (i.e., polyhydroxybutyrate (PHB) matrix, polyhydroxyalkanoates (PHA) granules, and cellulose binding module (CMB)). However, these devices and techniques have limitations and disadvantages.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 2A-2C illustrate a cross-sectional side view of different embodiments of bipolar electrode (BPE) devices.

FIG. 3B shows a series of BPE separators.

FIG. 3C shows an embodiment of a cascade of series and parallel BPE separators.

DETAILED DESCRIPTION

Figure 1:
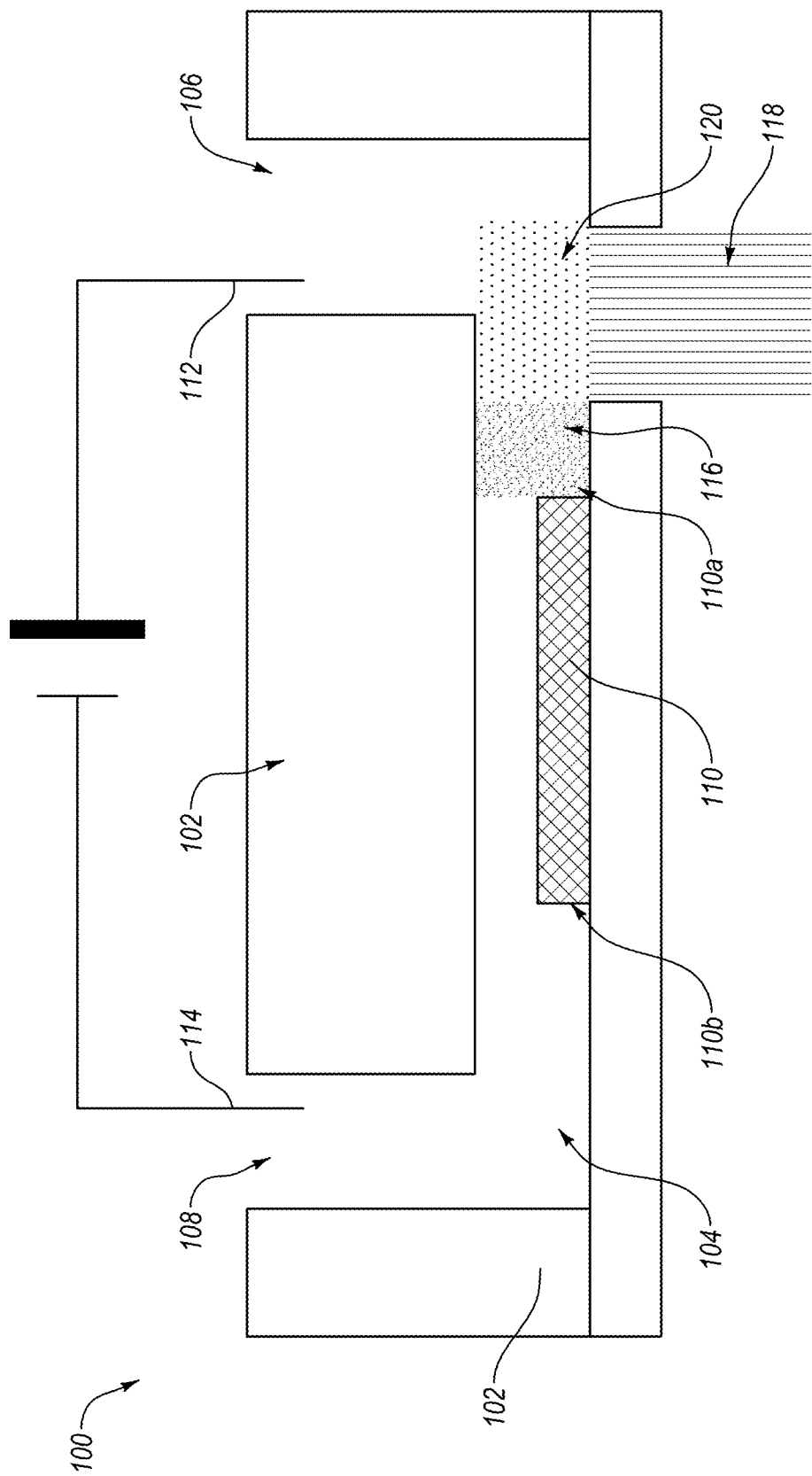
FIG. 1 illustrates a cross-sectional side view of an embodiment of a bipolar electrode (BPE) device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to fluidic devices that use a bipolar electrode (BPE) to generate a depletion zone that causes analytes to be inhibited from traversing the depletion zone and BPE. A bipolar electrode is an electrode that functions as the anode of one cell and the cathode of another cell. The BPE can be formed into a wall of a fluidic channel. Alternatively, the BPE can have through holes or apertures or pores and form a BPE barrier across the fluidic channel, where the dimension of the through holes or apertures or pores can determine the analytes that can traverse therethrough or be caged (e.g., held and not allowed to traverse the BPE) when the BPE is activated or deactivated. The fluidic BPE devices can be configured to be used in batch and/or continuous mode for selection of analytes, concentration of analytes, and purification of analytes or fluids. In one aspect, the BPE can extend across a main channel to concentrate the analyte in the main channel or allow the analyte to enter a side channel upstream of the BPE. The leading edge or upstream edge of the BPE can be from perpendicular to the longitudinal axis of the main channel or at an angle with respect thereto. In one aspect, the BPE can extend partially or fully across the main channel. In one aspect, the BPE can extend partially into the main channel to deflect the analyte. In one aspect, two BPEs can be on opposite sides of the main channel with a space therebetween. In one aspect, a main channel can have a plurality of BPEs and associated side channels.

The BPE can be a permeable BPE. A permeable BPE can be a metallic permeable material (e.g., meshes or porous materials) that can be used as the BPE electrode. The electrode can be at an angle (e.g., orthogonal) to the flow direction. The permeable BPE can extend across the flow direction as a barrier to fluid flow, where the fluid can flow through the through-holes, aperture, or pores therein. The permeable BPE can be polarized to generate a depletion zone that causes analytes to be inhibited from traversing the depletion zone and BPE.

The BPE can be an impermeable BPE. An impermeable BPE can be a solid, planar electrode formed on the channel wall. The BPE electrode surface can be planar and parallel to the direction of the fluid flow. The leading edge of the BPE can be at an angle (e.g., orthogonal) to the flow direction while on the channel wall. The impermeable BPE is not used as a barrier to fluid flow.

In one embodiment, a sample preparation device can use a permeable BPE sandwiched between an anode and a cathode for high-throughput sample preparation (e.g., separation and preconcentration) and/or decontamination of molecular and particulate samples. The sample preparation device can be operated in both the batch-mode (e.g., one inlet and one outlet) and continuous-mode (e.g., one inlet and at least two outlets—one concentrate outlet and one filtrate outlet). The performance of the sample preparation device (e.g., concentration/filtration ratio) can be adjustable via modulation of the applied electric field and flow split ratio.

In one embodiment, a sample preparation device can use a BPE sandwiched between an anode and a cathode and adjacent to a side channel for continuous high-throughput sample preparation (e.g., continuous separation and preconcentration) and/or decontamination of molecular and particulate samples. The concentrated analyte can be withdrawn continuously from the side channel. The sample preparation device can include a main channel with one inlet and one outlet and at least one side channel with one outlet upstream from at least one BPE. The BPE can be permeable or impermeable. At least one BPE can be deployed downstream of the side channel between the main channel inlet and main channel outlet with a certain angle (e.g., 10-90 degrees) with respect to the flow direction. The BPE force experienced by the analyte (e.g., cells, particles or molecules) is sufficient to counteract the hydrodynamic force. Thus, the analyte will be excluded from approaching the BPE and is diverted into one of the side channels for preconcentration or separation.

In one embodiment, a sample preparation device can be configured as a focuser that includes a main channel with one inlet and one outlet, and at least one pair of side channels with at least one pair of BPE electrodes (e.g., permeable or impermeable) located at the intersection of the main channel and the at least one pair of side channels. The pair of side channels are located opposite from each other across the main channel. The pair of side channels are subject to the electric field to activate each BPE. The pair of BPEs at the side channels can be arranged with a surface at an angle (0<theta<90) with respect to the flow direction to form a non-overlapped depletion zone and exclusion force onto molecular and particulate samples for focusing. The width of focused sample stream is rendered tunable via modulation of the flow and/or electric field settings. The BPEs can be planar or barrier oriented.

FIG. 1A illustrates a BPE selector 100 configured to select certain substances from a fluid. The BPE selector 100 includes a body 102 defining a fluid channel 104 that has an inlet 106 and an outlet 108 with a BPE 110 located between the inlet and the outlet. The BPE 110 is located on one or more of the walls of the body 102. While shown to be on a bottom wall, the BPE 110 can be on side walls and/or top wall. While shown as a flat substrate on the bottom wall, the BPE may be a member with apertures that extends across the fluid channel 104 so that the apertures are longitudinal with the fluid flow so that fluid can pass through the aperture from one side of the BPE 110 to the other side. The inlet 106 is shown to have an anode 112, and the outlet is shown to have a cathode 114. The orientation of the anode 112 and the cathode 114 facilitates the properties of the BPE 110. The BPE 110 can be a metallic member such that it functions as a BPE cathode 110a with respect to the anode 112 and a BPE anode 110b with respect to the cathode 114.

The BPE selector 100 is utilized to concentrate and separate molecules and cells that are applied to the inlet 106. The BPE selector 100 utilizes ion exclusive depletion phenomenon caused by the strong, non-uniform electric field around the BPE 110 under a sufficiently high, externally applied electric field $E_{Total}$ across the fluid channel 104 (e.g., microchannel). A non-uniform field is caused by the Faradaic reactions on the BPE 110 due to the BPE 110 polarization. The homogeneous reaction adds OH− and H+ to the local aqueous solution, which increases the conductivity near the poles of the BPE 110 and changes the electric field profile. In turn, this results in the formation of an electric field gradient, generating an exclusive depletion zone 116 near the edge of the BPE 110 and exerting an exclusive force on ions, molecules, or particles in the fluid. The depletion zone 116 causes the particles to concentrate upstream, which results in a concentration zone 120 that has a high concentration of particles. While some particles may traverse the depletion zone 116 and the BPE 110, the majority of particles do not enter the depletion zone 116, which causes the high concentration zone 120 to increase in concentration as more fluid flows through the fluid channel 104.

Accordingly, the body 102 may define one or more concentration zone outlets 118 adjacent to the BPE 110. When there are one or more concentration zone outlets 118 adjacent to the BPE 110, the device can be used as a continuous BPE selector when the fluid is collected from the concentration zone 120. The one or more concentration zone outlets 118 can be holes and/or channels at any angle with respect to the longitudinal wall.

Experimental demonstrations were performed on the BPE selector 100 as a microfluidic platform to select particles in fluid flow by using the BPE selection technique for substance (e.g., molecule, particle, and cell, etc.) concentration. The BPE selector 100 can be configured to operate in a batch mode by either not including the concentration zone outlets 118 or they are closed (e.g., with a valve). The BPE selector 100 can be configured to operate in continuous mode by including the concentration zone outlets 118 in an open orientation.

An aqueous solution containing microparticles (e.g., 2 microns) is introduced into the inlet 106 and flows through the fluid channel 104 to the outlet in batch mode. Visualization of the particles in the fluid flow through the fluid channel is conducted with the BPE 110 activated or deactivated. When activated, the BPE 110 generates a flow barrier depletion zone 116 that inhibits the particles from flowing past the BPE 110 and causes the particles to concentrate in the concentration zone 120. As such, the concentration zone 120 experiences particle concentration increases while the BPE is activated. When deactivated, the BPE 110 does not inhibit particles from traversing, and the particles flow to the outlet 108. The particles can be collected from the concentration zone 120 by flowing the fluid through the fluid channel 104 and the particles can be collected at the outlet 108 and analyzed.

This allows for selective barrier generation to retain substances from the fluid flow, and selective barrier removal to allow for the selective collection of substances. Turning the electric field off acts as a release for the collected substance.

The device can include the concentration zone outlets 118 and be used in a continuous manner. Particles flow in the fluid channel 104 with the BPE 110 deactivated, and the particles are collected at the outlet 108. When the BPE 110 is activated, the particles are collected from the concentration zone outlets 118.

Figure 6A:
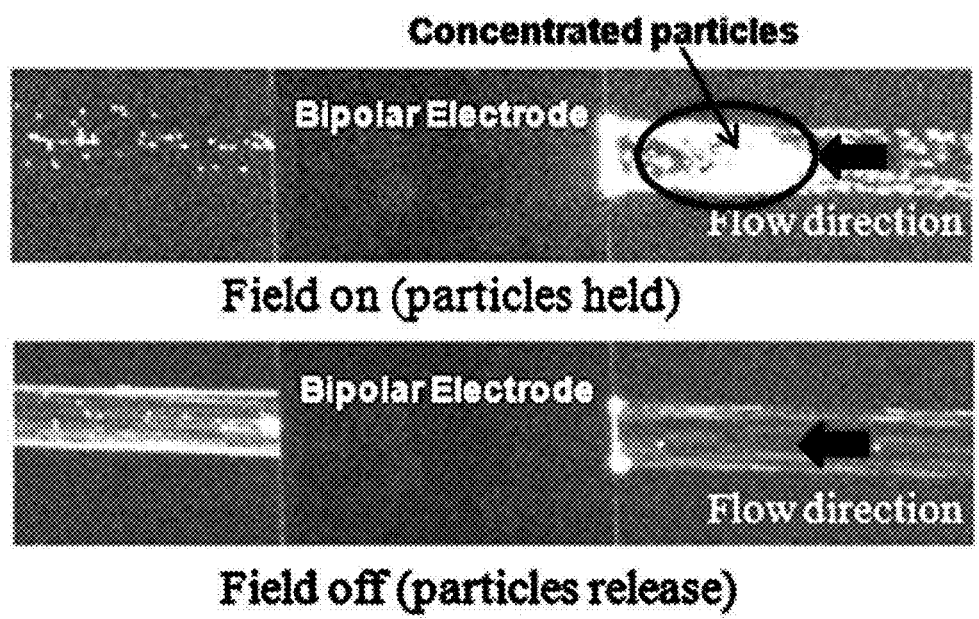
FIG. 6A includes micrographs showing BPE activation for particle caging and deactivation for particle release in a batch mode.
Figure 6B:
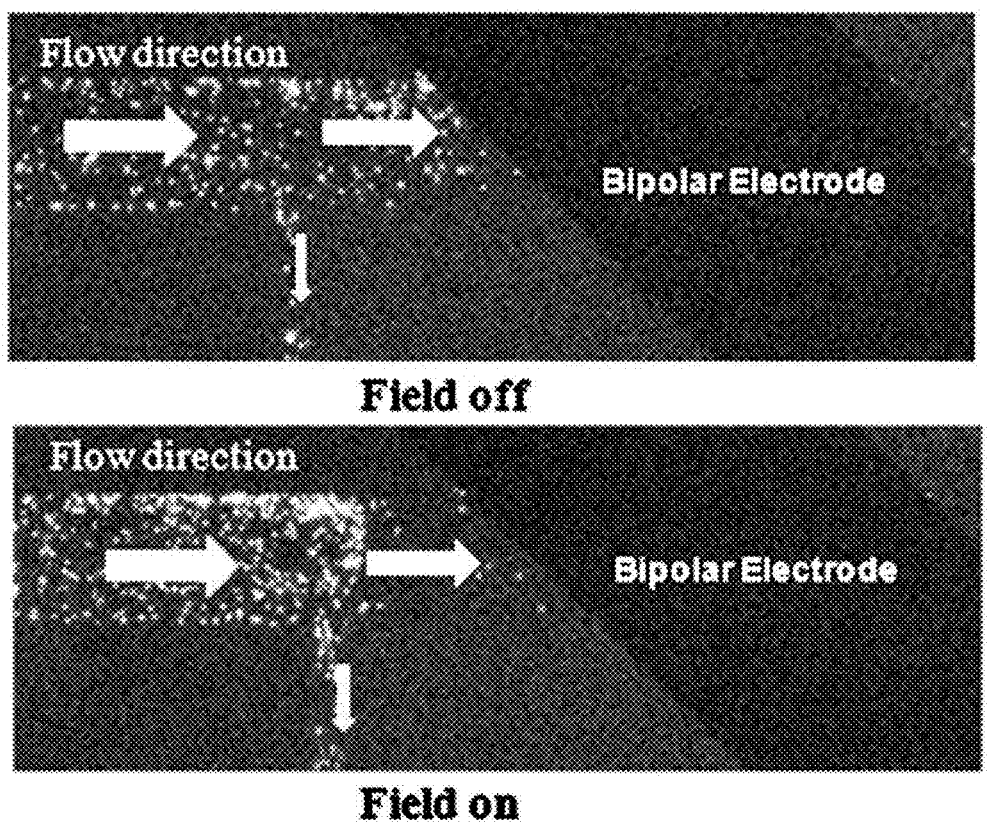
FIG. 6B includes micrographs showing BPE activation for particle caging and redirecting for preconcentration of particles in continuous mode.

FIGS. 6A and 6B exhibit the concentration of 2-μm particles in the batch mode and continuous mode, respectively. In batch mode (with the concentration zone outlets 118 closed), the particles are concentrated and gathered in front of the BPE 110 when the field is turned on, and the concentrated particles are released when the electric field is turned off. A T-type channel (e.g., the concentration zone outlets 118) with the BPE 110 located at the immediate downstream of the junction is used in the continuous mode setup. The particles are excluded from traversing the BPE 110 and concentrated in the concentration zone 120. The concentrated particles exit the fluid channel 104 through the concentration zone outlets 118 into side channels when the electric field is turned on. The concentration zone outlets 118 allow for continuous operation because the particles can be continuously selected and removed through the side channels.

In one embodiment, the BPE selector can exclude glass scaffolding layers that are found in DEP-CF preconcentrators, which have been determined to be fragile, expensive, and difficult to uniformly manufacture.

In one embodiment, the BPE selector can include a BPE that is plate, apertured substrate, grid, or mesh.

In one embodiment, the BPE selector can operate at voltages less than 300 V, more preferably less than 200 V, and even more preferably less than 150 V. Unlike the DEP-CF preconcentrator, the BPE selector does not require a high voltage (300-700 V) for effective concentration because Faradaic reactions can occur at lower voltage range (100 V), and higher voltages may, in fact, impede performance by causing bubble formation due to hydrolysis. As such, the BPE can operate at voltages less than 100 V.

FIG. 2A illustrates an embodiment of a BPE selector 200a that includes several structural and functional layers sandwiched between two polycarbonate plates (e.g., hard casing). The components of the BPE selector can be assembled, from top down, in the following order: (1) a hard casing layer 210, (2) a rubber gasket 212, (3) a top electrode 214, (4) alternating layers of three rubber gaskets 216 with a chamber cutout 218 and two wire mesh layers 220 that extend across the chamber cutout 218, (5) a bottom electrode 222, (6) a rubber gasket 224, and (7) a bottom hard casing layer 226. The two wire mesh layers are connected via an electrical connector 228 (e.g., copper tape) through a cutout in the middle rubber gasket 216. A flow channel 230 extends from an inlet 232 to the chamber cutout 218 and out an outlet 234. The wire mesh layers 220 are permeable barriers across the flow channel 230; however, other permeable barriers with through-holes or apertures can be used. The outlet 234 can include a valve 236 so that fluid flow out the outlet 234 can be sent out a waste container 238 or to a collection container 240. The BPE selector 200 can be dimensioned to be microfluidic (e.g., less than a mm) or macrofluidic (e.g., greater than a mm).

The BPE selector is operated in batch mode. The batch-mode operation of the BPE selector can include two steps: (1) Caging phase; and (2) Flush phase. The caging phase includes the sample solution being loaded into a first chamber 218a with the electric field activated (e.g., at the top-bottom electrodes 214, 222). The wire mesh layers 220 are polarized and the ion exclusion layer along with the high electric field gradient is generated at the front of the wire mesh layers 220 in the first chamber 218a. The particles are excluded from entering the wire mesh layers 220 (which can be substituted with any substrate having through-holes) due to the non-uniform electric field gradient leading to the accumulation and enrichment of the particles in the first chamber 218a, while water traverses the wire mesh layers 220 and is collected in the waste container 238. Due to the exclusion depletion zone near the wire mesh layers 220, the excluded particles are suspended above the wire mesh layers 220 (e.g., wire mesh barrier layer) without contact with the surface (i.e., contactless concentration). The flush phase can include flushing the particles from the first chamber 218a. Once all the sample volume is processed, the electric field can be turned off. Air or a small amount of water (e.g., DI water) is then pumped into the inlet 232 through the flow channel 230 to drive all the enriched particles through a second chamber 218b and through a third chamber 218c to the collection container 240.

Also, a first side channel 242 can be fluidly coupled to the first chamber 218a, which allows for particles trapped in the first chamber 218a to be obtained in a continuous mode.

FIGS. 2B and 2C show embodiments of batch and continuous mode BPE preconcentrators 200b, 200c. The BPE preconcentrators include: a sample inlet 250; a sample chamber 252 having a first electrode 254 on one side and a metallic mesh 256 on the other side; a discharge chamber 258 on the other side of the metallic mesh 256 (e.g., having through-holes or pores 257) and having a second electrode 260 on the opposite wall; and a filtrate outlet 262. The difference is that the continuous mode BPE preconcentrator 200c has a concentrate outlet 242 not present in the batch mode BPE preconcentrator 200b. The figures show the BPE force and hydrodynamic force that impacts the particles in the sample. A depletion zone 264 is in the sample chamber 252 adjacent to the metallic mesh 256.

The substances (e.g., chemicals, particles, cells) are completely excluded from entering the depletion zone and are enriched in a point-wise, static region in front of the depletion region. The large-size metallic mesh in a macro-scale fluidic platform can achieve: (1) concentration of targets, such as ions, molecules (e.g., nucleic acids and proteins, etc.) and particles (including biological cells, spores, and dusts, etc.); and (2) removal of the undesirable contaminants from the liquid medium. For charged ions and molecules the manipulation arises from the electrostatic force and electrophoresis, while for neutral molecules or particles it is contributed by the dielectrophoresis due to the large electric field gradient in front of the BPE mesh. Due to the distinctly different physical (size and shape), electric, and dielectric properties (electric charge, structure, conductivity, and permittivity) of targets and non-targeted contaminants, the externally applied electric field and electric conductivities of the sample solution can be adjusted to modulate the exclusive force on the ions, molecules, and particles for selective preconcentration and decontamination.

FIGS. 2A-2C illustrate the schematic of the BPE preconcentrator device that includes three key components: Two macrofluidic, cross-flow chambers: a sample chamber and a filtrate chamber; a metallic mesh with a large array of through holes, which separates the sample and filtrate chamber; and a pair of electrodes are placed in each chamber, respectively.

The liquid sample introduced into the device is powered by a pump. An electric potential is then applied between the top and bottom electrodes yielding strong electric field across the metallic mesh. The field polarizes the mesh and forms a thin exclusion layer at one side of the mesh based on the BPE principles described above. The BPE exclusion force balances or overwhelms the hydrodynamic force and prevents the molecules or particles from traversing the holes in the mesh. Depending on the application, either the filtrate can be collected (i.e., filtration) or the retentate can be harvested by flushing (i.e., preconcentration). Preconcentration of the particles (yeast cells) and decontamination of the food dye (red and carrying negative charges) from water samples using the BPE-based device are performed with preconcentration occurring when the electric field is on and not occurring when the electric field is off. In addition to the batch-mode operation in 2B, the device can also be operated in the continuous-mode as shown in FIG. 2C, where an outlet is added in the sample chamber, and the sample flow can be split into two streams. The forward (left-to-right) component of the hydrodynamic force in the sample chamber carries the retentate towards the outlet. Simultaneously, a major portion of the solution (i.e., filtrate indicated by the arrows) is diverted to the filtrate chamber and purged out. The continuous-mode decontamination of the negatively-charged food dye is conducted in the continuous-mode, where the food dye is obtained as the retentate and a clear liquid is obtained as the filtrate.

The disclosed technology features three primary innovations: (a) use of the metallic mesh as the BPE for macro-scale, high-throughput sample preparation and decontamination of both molecular and particulate samples in both the batch-mode and continuous-mode; and (b) the operation and preconcentration/filtration ratio are rendered adjustable via modulation of the applied electric field and flow split ratio. Technology benefits include: (a) pronounced field-portability (simple principle and device configuration, minimized size, weight, and power requirement); (b) filter-free operation and high recovery efficiency; (c) robustness to clogging and biofouling; and (d) salient scalability with multiple preconcentrator units can be connected in parallel or in cascade to scale up the throughput and concentration factors for a single pass.

Figure 3A:
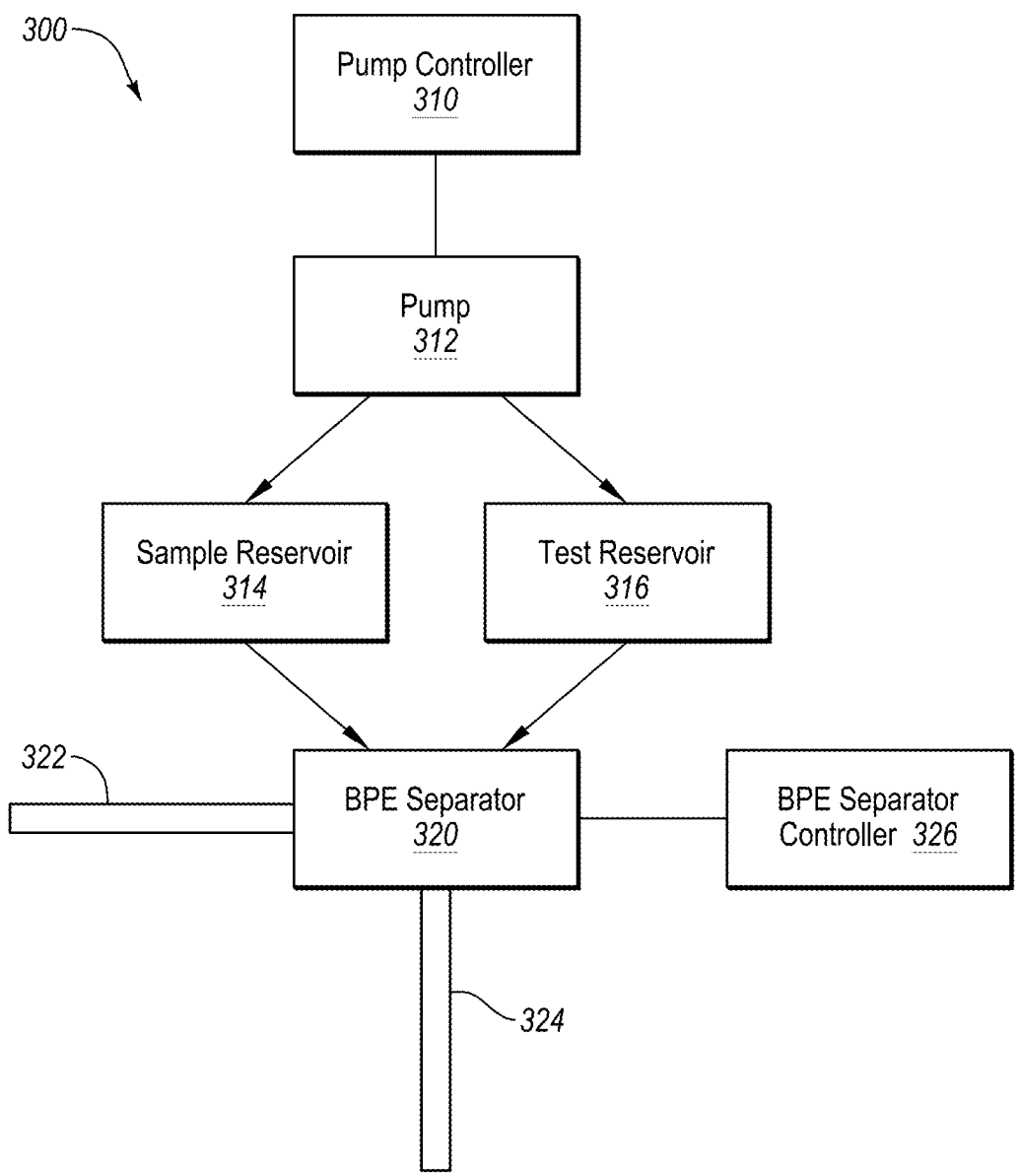
FIG. 3A illustrates an embodiment of an analyte selection system that includes a BPE separator.

FIG. 3A shows a BPE concentrator system 300 that includes a pump controller 310 operably coupled with a pump 312 that is operably coupled with a sample reservoir 314 and a test reservoir 316. The sample reservoir 314 and the test reservoir 316 are fluidly coupled with a BPE separator 320. The BPE separator includes a concentrator outlet 322 and a diluted outlet 324. The BPE separator 320 is operably coupled with a BPE separator controller 326.

FIG. 3B shows a series or cascade of BPE preconcentrators 360. FIG. 3C shows parallel BPE preconcentrators 370.

The end product of the BPE devices can be compact, integrated, field portable devices for high-throughput, filter-free, selective liquid sample concentration or decontamination. Due to the high throughput and pronounced fieldability, scalability, and integrability, the device will be suited for integration with a diversity of next-generation bioanalysis and detector systems as well as mission support equipment. The developed technology will have applications in a variety of global markets including pharmaceutical, biotechnology, medical, health care, environmental evaluation, water monitoring and purification, forensics, and biodefense. Other adoptees of the technology include biomedical, biological labs and universities/non-profit centers for clinical diagnostics and ecology research. The device design can include a top/bottom electrode pair, a macro-size metallic mesh, and two separate fluidic chambers. Exposure of the metallic mesh between the two macro-size electrode pair forms metallic mesh polarization-induced electric force. Large hole sizes in the metallic mesh can be used to mitigate the clogging and biofouling issues in contrast to the conventional membrane systems. Continuous-mode BPE sample preconcentration and decontamination devices can be used. Manipulation of the applied electric potential and flow split ratio can be performed for adjustable preconcentration or decontamination ratio and throughput. Multiple units connected in a serial or parallel manner can be used to achieve accumulative preconcentration/decontamination or further elevate throughput.

In one embodiment, the present invention can include a continuous-mode fluidic focuser for biological and chemical sample preparation. The underlying principle of the fluidic focuser device is based on the formation of a depletion zone formed by the use of an asymmetric electric field in a microchannel containing a BPE. The asymmetric electric field arises from the local increase in electrical conductivity in the microchannel caused by Faradaic reactions at the BPE. Specifically, when a strong enough electric field is applied across the microchannel, Faradaic reactions are taking place at the BPE. As normally configured, the products of the reactions are $OH^-$ (at the cathodic pole of the bipolar electrode) and $H^+$ (at the anodic pole of the bipolar electrode); i.e., the products of hydrolysis. The homogeneous reaction adds $OH^-$ and $H^+$ to the local media, which increases the solution conductivity near the poles of the BPE and changes the electric field profile within the microchannel. In turn, it results in the formation of an electric field gradient, generating a depletion zone near the edge of the BPE and exerting an exclusive force on molecular or particulate samples. The fluidic focuser harnesses lateral, weakly overlapped (or non-overlapped) depletion layers to achieve concurrent analyte enrichment and focusing/pinch in a continuous mode.

Figure 4A:
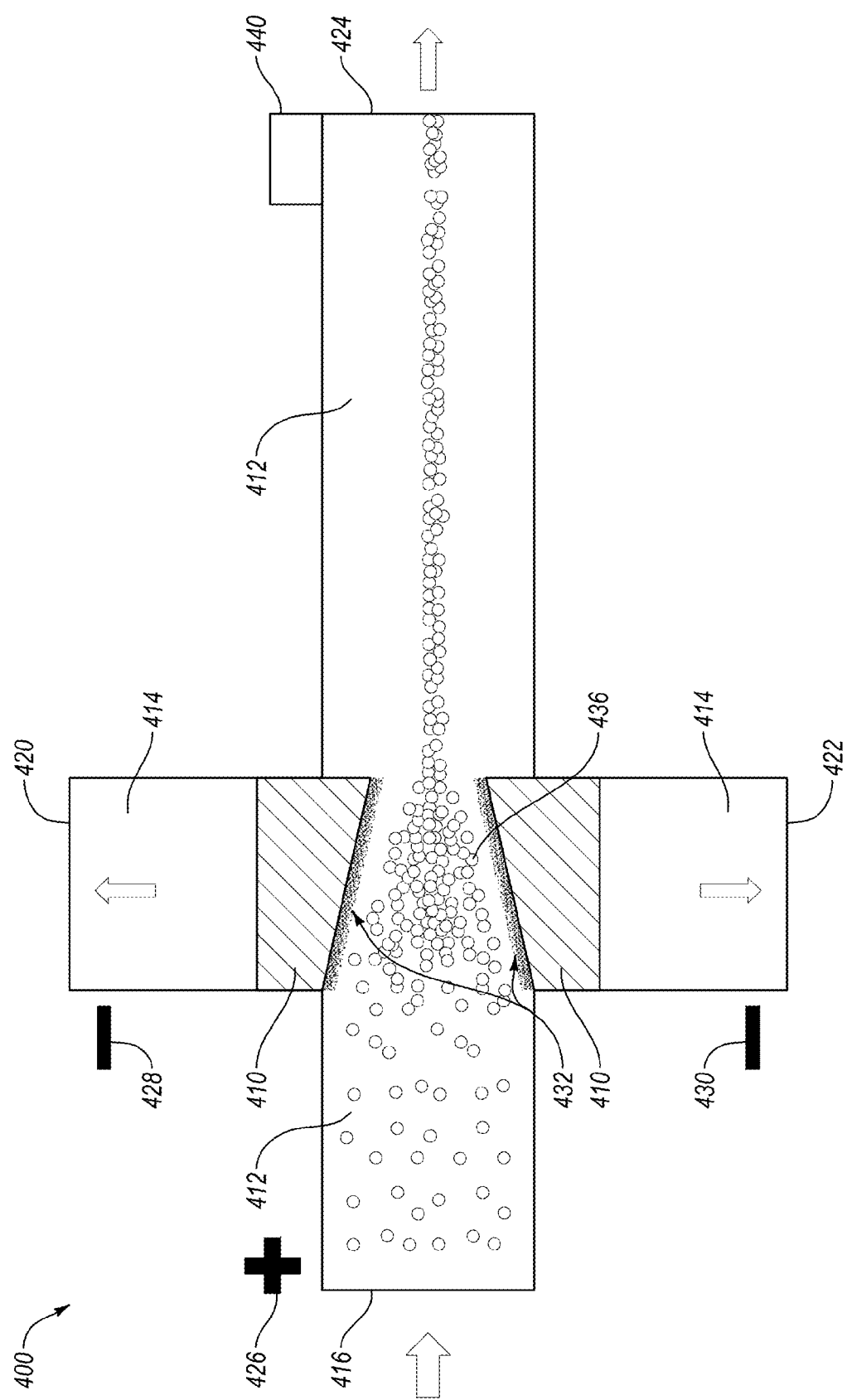
FIGS. 4A and 4B illustrate embodiments of BPE focusing concentrators/separators.

FIG. 4A shows a schematic of a fluidic BPE focuser 400 that uses continuous-mode focusing and preconcentration of analyte utilizing two BPEs 410. The fluidic focuser 400 contains a main microchannel 412 connected to two side channels 414. Two BPEs 410 are place at the interface between the main channel 412 and the side channels 414 with each BPE 410 at an appropriately selected angle. The sample enters the device from the inlet 416 and then exits from the outlets (e.g., first side outlet 420, second side outlet 422 and/or main outlet 424). Upon application of electric potential $V_1$, $V_2$ and $V_3$ at the anode 426 (V1) at inlet 416, cathode 428 (V2) at first side outlet 420 and cathode 430 (V3) at second side outlet 422 respectively, such that $V_1>V_2$ and $V_1>V_3$, two depletion regions 432 are formed at the main-side channel interface 436 of each BPE 410, which exerts exclusive force on the target analyte (e.g., cell, particulate or molecular) so as to overwhelm the lateral hydrodynamic force. Thus, the analyte is excluded from entering the side channels 414 and focused towards the center of the main channel 412 as it moves along the electrode. The solution diverted into the side channel 414 is analyte-free yielding higher analyte concentration in the main channel 412. Furthermore, as the depletion regions 432 are only weakly overlapped (or even non-overlapped) at the center of the main channel 412, the analyte can escape the electrode region and flow downstream along the main channel 412 to enable continuous focusing and concentration. The enriched and focused analyte then can be detected and analyzed by downstream sensors 440. The width of the focused analyte stream can be adjusted by manipulating flow (e.g., total flow rate and flow split ratio) and/or electric field (potential or current at the inlet and outlets). Large gradient across the electrodes will increase the exclusive force and further yield a more focused analyte stream.

The fluidic BPE focuser 400 features two primary innovations: (a) weakly overlapped (or non-overlapped) ion depletion layers used to enable continuous concentration and focusing of samples as opposed to existing batch-mode operation; and (b) the width of focused sample stream is rendered tunable via modulation of the flow and/or electric settings. The BPE focuser 400 benefits include: (a) simple operation (one-step, continuous mode); (b) salient tunability for sample focusing and preconcentration; and (c) marked integrability with lab-on-chip systems, in particular, with other electrokinetic systems (e.g., electrophoresis and impedance detection) and bio-assays that needs sample-pretreatment for improved performance.

Figure 4B:
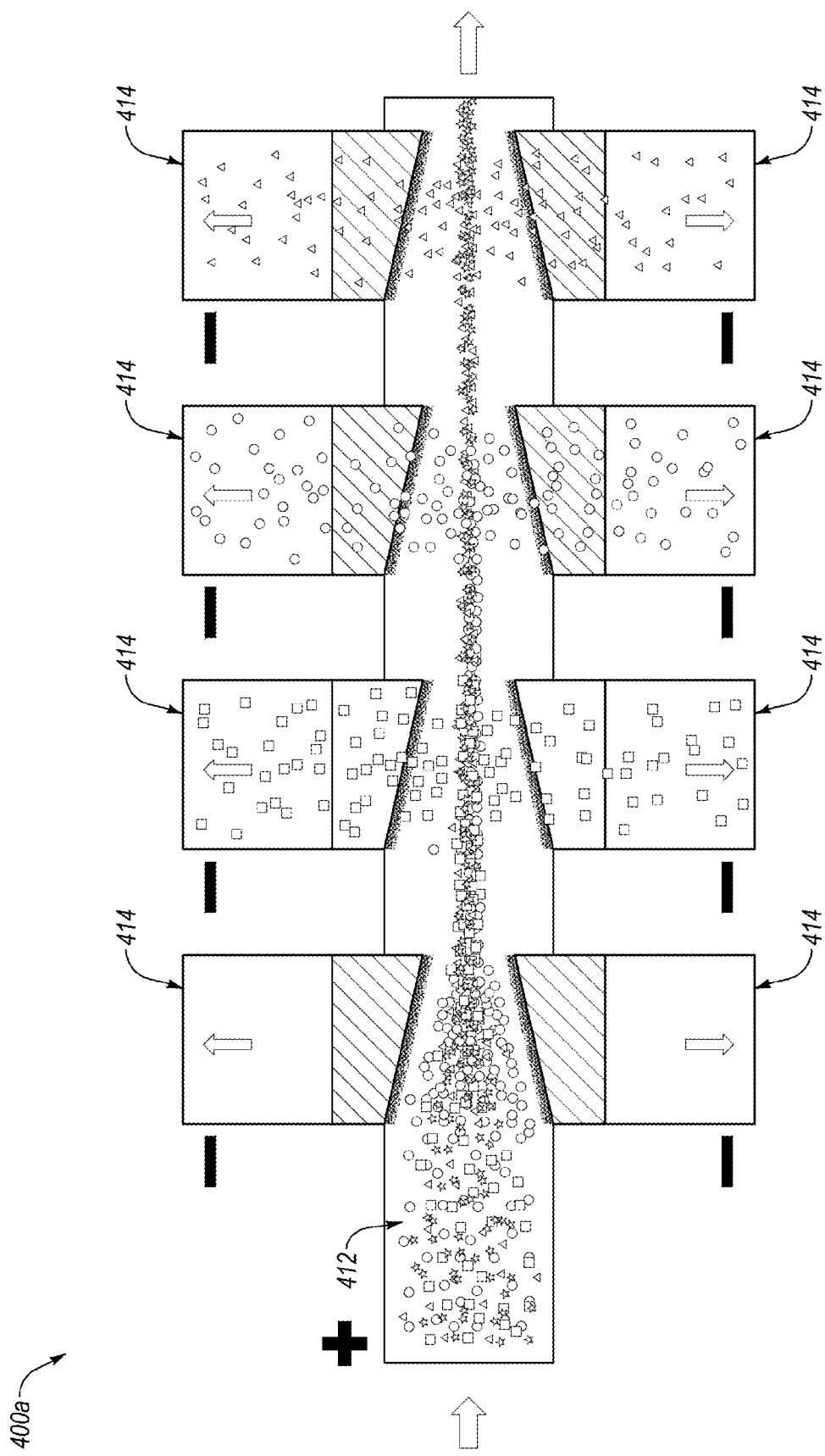

In one embodiment, a fluidic BPE focuser 400b can include a plurality of side channels 414 and a plurality of planar BPEs 410 each located at the interface between the main microchannel 412 and the individual side channels 414. This is shown in FIG. 4B.

The end product of the fluidic BPE focuser 400 will be a compact, tunable, continuous sample preconcentrator and focuser for integrated biofluidic instruments and sensors. The technology will find widespread applications, in particular, in the biodefense and biodiagnostics arena. Due to the high degree of adjustability and integrability, the fluidic BPE focuser 400 will be suited for integration with a diversity of next-generation, microfluidic/miniaturized analysis systems. The fluidic BPE focuser 400 will have applications in a variety of global markets including pharmaceutical, drug discovery, biotechnology, medical, health care, and forensics. Other adoptees of the technology include life sciences and biomedical labs and universities/non-profit centers for proteomics, genomics, and diagnostics research. The fluidic BPE focuser 400 can be configured for continuous-mode operation of bipolar electrode-based sample focusing as well as preconcentration. Manipulation of the weakly overlapped (or non-overlapped) depletion layer by the BPEs 410 can be used for continuous analyte preconcentration. Modulation of flow and electric configurations can be conducted for tunable preconcentration/enrichment ratio and throughput.

In one embodiment, a fluidic analyte preconcentration and focusing apparatus can include: a main flow channel having an inlet and an outlet, side flow channels, and planar bipolar electrodes placed at the interface between the main channel and the side channels with an appropriately selected angle. That is, the angle can vary. The fluidic analyte preconcentration and focusing apparatus can include a main channel, a plurality of side channels, and a plurality of planar bipolar electrodes (each located at the interface between the main channel and the individual side channel).

The BPE focusing device can be used similar to the BPE concentrator and can be used in the same methods and same systems, such as in FIGS. 3A-3C. The BPE focuser can be used for focusing, concentration, and purification, etc.

In one embodiment, a BPE device can harness the exclusive BPE force to achieve (1) separation and concentration of both molecular samples (e.g., nucleic acids and proteins, etc.) and particles (including biological cells, spores, etc.); and (2) continuous-mode operation for high throughput processing and concurrent detection. The present invention contains a main microchannel connected to a side channel. The BPE is placed in the main channel, slightly downstream of the side channel. The sample-laden solutions are supplied via the main channel inlet and split into two streams towards the side channel outlet and the main channel outlet, respectively. Upon application of the electric field E across the main channel, the depletion region is formed in front of the embedded BPE to generate an exclusive force on the sample.

Figure 5A:
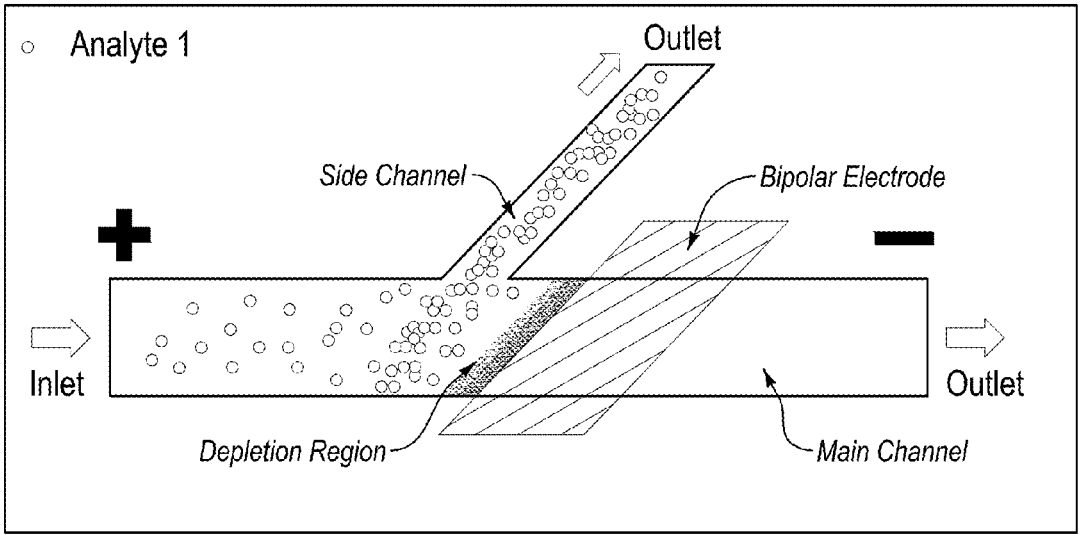
FIGS. 5A and 5B illustrate embodiments of BPE focusing concentrators/separators.
Figure 5B:
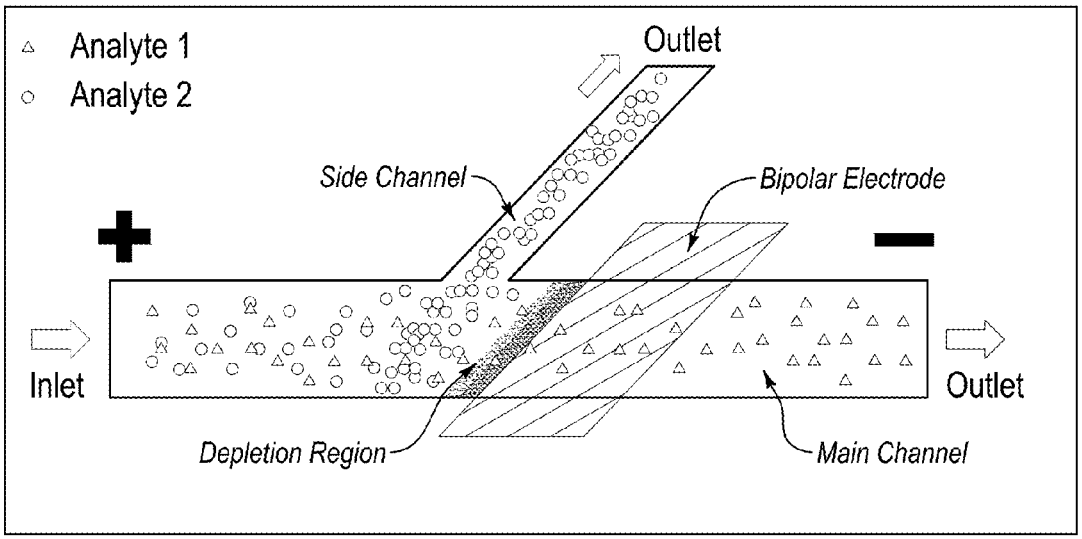

The BPE devices operate in two modes: (1) preconcentration mode (FIG. 5A) and (2) separation mode (FIG. 5B). In the preconcentration mode, the external electric field is tuned such that the exclusive force experienced by the analyte (particles or molecules) is sufficient to fully counteract the hydrodynamic force. Thus the analyte is excluded from approaching the BPE and is diverted into the side channel. The side channel can be at any angle with respect to the main channel, such as from 45 degrees to 90 degrees or 10 degrees. Only a fraction of the solution flows into the side channel, leading to the reduction in the liquid volume and high analyte concentration therein. The enriched sample is continuously transported downstream for detection and analysis. By controlling the flow split ratio between the main channel and the side channel, different concentration ratios can be attained.

Since various analytes have unique electric properties (i.e., electric charge, electric conductivity, and particle size) and dielectric properties (e.g., permittivity), the exclusive forces acted on them are different, which can be harnessed for separation. Consider a solution containing two analytes (analyte 1 and analyte 2 in FIG. 5B), the BPE exclusive force is sufficient to completely balance the longitudinal hydrodynamic force for analyte 1 but insufficient for analyte 2. This differential response can be attained by tuning the flow rate and/or the electric field. As a result, analyte 1 will be diverted into the side channel while analyte 2 will remain in the main channel, leading to separation of analyte 1 from analyte 2. The purity of analyte 1 relative to analyte 2 in the side channel can be adjusted by varying the flow split ratio. A plurality of side channels can purify a plurality of analytes from each other.

The BPE devices can include: (a) continuous operation or batch mode; (b) preconcentration and separation of both molecular and particulate samples; and (c) the operation and enrichment ratio are rendered adjustable via modulation of the flow split ratio and applied electric field. The BPE devices can provide: (a) simple operation (one-step, continuous mode); (b) salient adjustability in concentration ratio, separation efficiency, and throughput; (c) ability to separate and concentrate multiple species with multiple devices in a series connection or parallel; and (d) marked integrability with lab-on-chip systems, in particular, with other electrokinetic systems (e.g., electrophoresis and impedance detection) and bioassays that need sample-pretreatment for improved performance. The BPE devices can be used in a compact, tunable, continuous sample preconcentrator and separator for integrated biofluidic instruments and sensors. The BPE devices can be used in widespread applications, in particular, in biodefense and biodiagnostics arenas. Due to the high degree of adjustability and integrability, the BPE devices can be suited for integration with a diversity of next-generation, microfluidic/miniaturized analysis systems. The BPE devices can have applications in a variety of global markets including pharmaceutical, drug discovery, biotechnology, medical, health care, and forensics. Other adoptees of the technology include life sciences and biomedical labs and universities/non-profit centers for proteomics, genomics, and diagnostics research. The BPE devices can include continuous-mode bipolar electrode-based sample separation devices and sample preconcentration devices that can perform manipulation of flow and manipulation of electric configurations for adjustable preconcentration/enrichment ratio and throughput. A fluidic BPE analyte preconcentration and separation apparatus can include: a main flow channel having an inlet and an outlet, a side flow channel having an outlet and appropriate intersection angle relative to the main channel, and a planar bipolar electrode located slightly downstream the side channel. A fluidic BPE analyte preconcentration and separation apparatus can include a main channel, a plurality of side channels, and a plurality of planar bipolar electrodes, each located slightly downstream of the individual side channel. Exposure of the BPE to the electric field can facilitate the methods of analyte selection described herein.

In one embodiment, an analyte selection device can include: a body defining a fluid channel having a channel inlet and a channel outlet; a bipolar electrode (BPE) between the channel inlet and channel outlet; one of an anode or cathode electrically coupled with the BPE on a channel inlet side of the BPE and the other of the anode or cathode electrically coupled with the BPE on a channel outlet side of the BPE; and an electronic system operably coupled with the anode and cathode so as to polarize the BPE. The fluid channel can have any shape or dimension. The channel inlet and channel outlet can be longitudinal or lateral with respect to the longitudinal axis of the channel. The BPE can be any metallic member, such as a flat plate on a wall or mesh as a barrier BPE. The anode and cathode can be located at a position that polarizes the BPE.

In one embodiment, the body can define a chamber having the BPE. The chamber can be fluidly coupled with the channel inlet and channel outlet so as to be located therebetween. The chamber can have a dimension larger than the channel. As such, the channel opens into the larger chamber. The chamber can have a concentrate portion between the channel inlet and BPE. The concentrate portion can be between an inlet into the chamber and the BPE. The chamber can have a filtrate portion between the BPE and channel outlet. The filtrate portion can be between the BPE and outlet of the chamber. One of the anode or cathode is in the concentrate portion of the chamber opposite of the BPE and the other of the anode or cathode is in the filtrate portion of the chamber opposite of the BPE so that the anode and cathode are on opposite sides of the chamber with the BPE therebetween.

In one embodiment, the analyte selection device can include a side channel fluidly coupled with the concentrate portion of the chamber. The side channel can be at a location opposite or away from the chamber inlet. In one aspect, the chamber inlet is on one side of the chamber and BPE and the side channel is on the opposite side of the chamber at the other end of the BPE. The BPE can extend across the chamber and form a barrier or partition to define the concentrate portion and filtrate portion. The chamber outlet can be opposite of the chamber inlet or across from the side channel on the opposite side of the BPE.

In one embodiment, the analyst selection device can include one or more side channels fluidly coupled with the fluid channel between the channel inlet and BPE. Any number of side cannels can be included. In some instances, side channel pairs can be located on opposite sides of the channel. The side channels may or may not include or be associated with a unique BPE.

In one embodiment, the BPE can be located anywhere along the fluid flow path. In one aspect, the BPE is located on a wall of the body, such as the bottom, sides, or top walls. Only one BPE can be included for causing the selection of analyte. The BPE can be planar so that the fluid flow passes thereover. As such, the BPE can be planar with respect to a fluid flow direction.

In one embodiment, the BPE can be a barrier BPE that inhibits fluid flow. The BPE can be a barrier BPE that extends between walls of the body so as to provide a barrier to fluid flow. The barrier BPE can have a plurality of fluid passages that fluidly couple the channel inlet side of the BPE with the channel outlet side of the BPE. The fluid passages can be pores, through holes, or apertures, or the like. The fluid passages can be large sized. For example, the fluid passages in the barrier BPE are less than or about 25 microns. The fluid passages can be small sized, such as when the analyte is smaller. For example, the fluid passages in the barrier BPE are less than or about 5 microns.

In one embodiment, the BPE can have different orientations with respect to the channel and fluid flow. In one aspect, a surface of the channel inlet side of the BPE is orthogonal with a direction of fluid flow. In one aspect, a surface of the channel inlet side of the BPE is at an angle with a direction of fluid flow (e.g., between 0 and 90 degrees).

In one embodiment, the analyte selector device can include: a first BPE on a first side of the channel and having a surface of a channel inlet side of the first BPE at a first angle with the channel; and a second BPE on a second side of the channel opposite of the first side and having a surface of a channel inlet side of the second BPE at a second angle with the channel. One or both the first BPE and second BPE can extend into the channel. In one aspect, the first BPE and second BPE are planar with respect to a direction of fluid flow in the channel.

In one embodiment, the analyte selector device can include a first side channel in the channel at the first BPE, and a second side channel in the channel at the second BPE opposite of the first side channel.

In one embodiment, the device can include a plurality of the first BPEs and first side channels and a plurality of the second BPEs and second side channels opposite of the first BPEs and first side channels. The device can include a plurality of BPEs between the channel inlet and channel outlet. In one aspect, each side channel may include a BPE of the plurality of BPEs, where the BPE can be downstream of the side channel or at the side channel.

In one embodiment, a voltage of from 50 V to 200 V is applied by the electronic system to the anode/cathode in order to cause polarization of the BPE.

In one embodiment, a pump is fluidly connected to the channel inlet. The pump can be configured to pump at 2 mL/minute to 10 mL/minute. A system can include the pump and analyte selector device.

In one embodiment, a BPE device can include a top/bottom electrode pair, a macro-size metallic mesh, and two separate fluidic chambers. Exposure of the metallic mesh between the two macro-size electrode pair can form metallic mesh polarization-induced electric forces. Large hole sizes in the metallic mesh can be included to mitigate the clogging and biofouling issues in contrast to the conventional membrane systems. The device can be configured for continuous-mode BPE sample preconcentration and decontamination methods. Manipulation of the applied electric potential and flow split ratio can be performed for adjustable preconcentration or decontamination ratio and throughput. Multiple BPE device units connected in a serial or parallel manner to achieve accumulative preconcentration/decontamination or further elevate throughput.

In one embodiment, a continuous-mode bipolar electrode based sample separation device and method can be provide.

In one embodiment, a continuous-mode bipolar electrode-based sample preconcentration device and method can be provided.

In one embodiment, manipulation of flow and electric configuration for adjustable preconcentration/enrichment ratio and throughput can be implemented on the BPE device.

In one embodiment, a fluidic analyte preconcentration and separation apparatus can include: a main flow channel having an inlet and an outlet, a side flow channel having an outlet and appropriate intersection angle relative to the main channel, and a planar bipolar electrode located slightly downstream the side channel.

In one embodiment, a fluidic analyte preconcentration and separation apparatus can include: a main channel, a plurality of side channels and a plurality of planar bipolar electrodes each located slightly downstream of the individual side channel.

In one embodiment, exposure of the planar bipolar electrode under electric field can facilitate the concentration and separation methods.

In one embodiment, a continuous-mode operation of bipolar electrode-based sample focusing device and method can be provided. The focusing device can be used as in continuous-mode operation of bipolar electrode-based sample preconcentration methods. The operation of the focusing device can include manipulation of weakly overlapped (or non-overlapped) depletion layer for continuous analyte preconcentration. Modulation of flow and electric configuration can be performed for tunable preconcentration/enrichment ratio and throughput.

In one embodiment, a fluidic analyte preconcentration and focusing apparatus can include: a main flow channel having an inlet and an outlet, side flow channels, planar bipolar electrodes placed at the interface between the main channel and the side channels with appropriately selected angle.

In one embodiment, a fluidic analyte preconcentration and focusing apparatus can include: a main channel, a plurality of side channels and a plurality of planar bipolar electrodes (each located at the interface between the main channel and the individual side channel).

In one embodiment, exposure of the planar bipolar electrode in the focusing device under electric field can facilitate the concentration and separation methods.

In one embodiment, an analyte selection device can include: a body defining a fluid channel having a channel inlet and a channel outlet; a bipolar electrode (BPE) between the channel inlet and channel outlet; one of an anode or cathode electrically coupled with the BPE on a channel inlet side of the BPE and the other of the anode or cathode electrically coupled with the BPE on a channel outlet side of the BPE; a side channel on the channel inlet side of the BPE; and an electronic system operably coupled with the anode and cathode so as to polarize the BPE. In one aspect, the BPE is located on a wall of the body. In one aspect, the BPE is planar with respect to a fluid flow direction.

In one embodiment, an analyte selection device can include: a body defining a fluid channel having a channel inlet and a channel outlet; a pair of side channels fluidly coupled with the channel and located on opposite sides of the channel; a pair of bipolar electrodes (BPE) between the channel inlet and channel outlet with one BPE of the pair at an intersection between the channel and side channel of the pair, the pair of BPEs including a first BPE on a first side of the channel and having a surface of a channel inlet side of the first BPE at a first angle with the channel and a second BPE on a second side of the channel opposite of the first side and having a surface of a channel inlet side of the second BPE at a second angle with the channel; one of an anode or cathode electrically coupled with the pair of BPEs on a channel inlet side of the BPEs and a pair of the other of the anode or cathode electrically coupled with the first and second BPEs on a side channel outlet side of the first and second BPEs; and an electronic system operably coupled with the anode and cathode so as to polarize the pair of BPEs. In one aspect, both the first BPE and second BPE extend into the channel from the pair of side channels. In one aspect, both the first BPE and second BPE are planar with respect to a direction of fluid flow in the channel.

EXPERIMENTAL

Both M. fujisawaense and C. metallidurans cultures were prepared mainly in two steps: (1) Cell Culture: 5 mL sterile nutrient broth was pipetted into each culture tube. Frozen stock was scrapped with a sterile loop into the culture tube and incubated at 30° C., 250 RPM for six hours. The inoculated broth was then transferred to a baffled flask containing 250 mL of nutrient broth, and incubated overnight at 30° C., 250 RPM. (2) Cell Preprocessing: 10 mL overnight cultured sample was pipetted into 10 mL tubes and centrifuged at 14,000 g for 20 min. The media was removed, and the pellet washed 1× with deionized water to remove any traces of nutrient broth, which has a high conductivity. Next, the concentrated sample was re-suspended in 120 mL of DI water to obtain the test sample at desired concentration ($10^6$ cells/mL).

An experimental protocol was performed for the macrofluidic BPE concentrator testing using the BPE concentrator system 300. Silicone tubing and adhesive alligator clips were used to connect the BPE separator to a syringe pump (fluidic) and the electrodes, respectively. The test sample (M. fujisawaense in DI water) was loaded into a 50 mL syringe and pumped through the macrofluidic BPE separator device at 2 mL/min during the caging phase. A DC electric field was generated using a Bio-Rad PowerPac high-voltage power supply. An air flush was performed using pressurized nitrogen gas, at 20 psi for five seconds. During the air flush phase 300-400 mL solution was collected at the concentrate outlet. In order to accurately calculate the input concentration supplied to the BPE separator, a side-by-side reference test using the same sample and the same syringe was employed to exclusively collect the inlet sample during the entire test.

Two types of tests were carried out in batch mode operation, including: (1) field-alternating tests; and (2) preconcentration tests to, respectively, examine the effect of exclusion zone and/or BPE and quantify the concentration ratio for different voltages.

Figure 7:
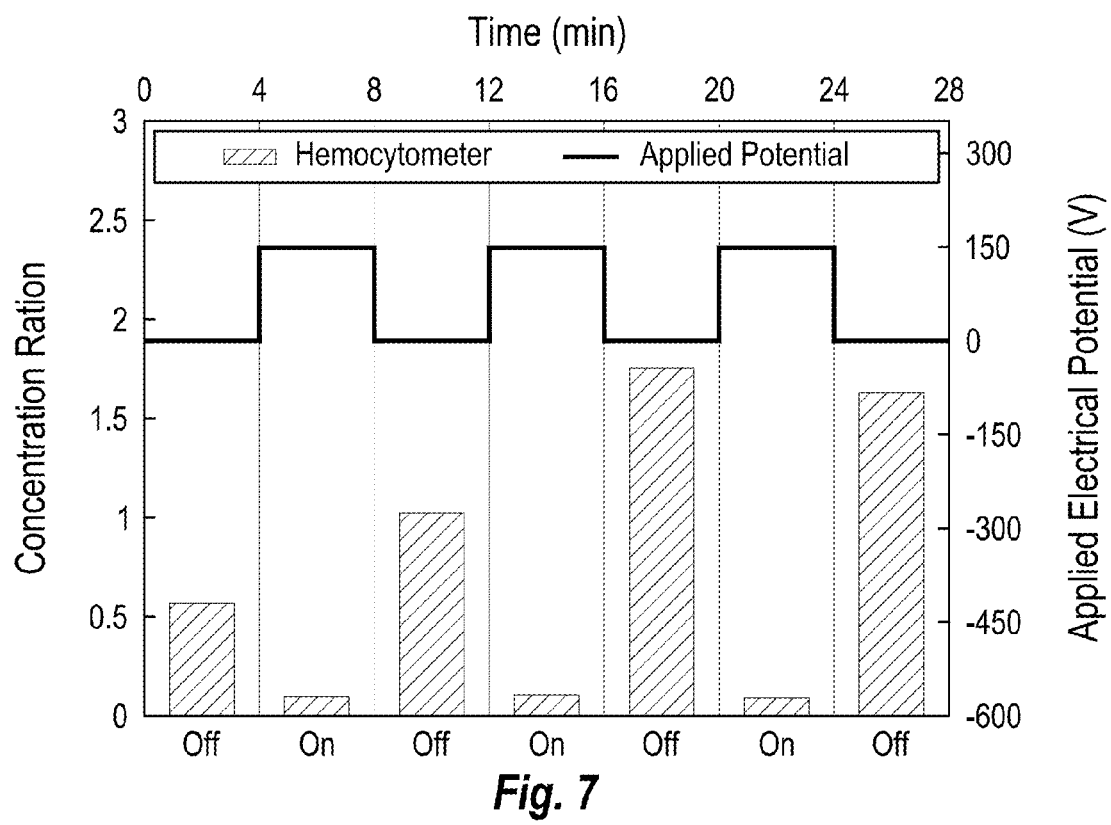
FIG. 7 includes a graph that shows the concentration ratio of the collected *M. fujisawaense* at the discharge outlet with an alternating electric potential.

In the field-alternating test, we alternated the electric field between on and off for three cycles, and each cycle lasted for six minutes. As such, the electric field was off for the time slots 0-4, 8-12, 16-20, 24-28 minutes, and on at 150 V for 4-8, 12-16, 20-24 minutes. The number of $M.$ $fujisawaense$ cells in the solutions collected at the discharge outlet during the "on" and "off" periods was compared to verify the effectiveness and caging capacity of the BPE exclusion zone. The sample was injected at 2 mL/min, and 8 mL was collected at the discharge outlet for each on/off period (e.g., four minutes). Samples were stained with SYTO® 9 and Propidium Iodide for visualization of bacteria and to facilitate hemocytometric counting. The number of $M.$ $fujisawaense$ cells in the collections was analyzed using a hemocytometer, and their concentration ratio (i.e., concentration relative to the inlet sample concentration) was measured using hemocytometer counts as depicted in FIG. 7. It was determined that the number of $M.$ $fujisawaense$ cells collected with the electric field activation was about one order of magnitude less than that in the field-off case (e.g., deactivation). The alternating tests illustrated the effectiveness of the electric field effect and BPE for excluding and caging the biological particles.

The preconcentration test was conducted upon verification of BPE exclusion of particles from traversal. The preconcentration tests followed the batch procedure (e.g., including a caging phase and a flush phase) to quantify the preconcentrator performance. A large volume (50 mL) of the $M.$ $fujisawaense$ sample was injected into the BPE preconcentrator at a flow rate of either 2 or 10 mL/min yielding an operating time of five or 25 minutes in the test. A DC electric field of 150 V was applied to the electrodes. About 400 μL of solution was collected at the concentrate outlet during the air flush phase, followed by an additional 300 μL water flush phase and additional air.

Hemocytometric and CFU images of the cell solution were collected at the inlet, discharge outlet, and concentrate outlet. Two different fluorescence dyes (SYTO® 9 and Propidium Iodide) were used to label the live cells and damaged cells, respectively. All the results matched very well and clearly exhibited an order-of-magnitude enrichment of the $M.$ $fujisawaense$ cells in the concentrate relative to the inlet sample (data not shown).

Table 1 delineates the discharge ratio (defined as the concentration at the discharge outlet over the concentration at the inlet) and concentration ratio for both the air flush and water flush concentrates, calculated from different counting methods (both hemocytometric and CFU count). An average of 12-14% cells (discharge ratio range from 0.122 to 0.135 for phase and CFU, respectively) escaped via the discharge outlet, which is comparable to the discharge percentage for the DEP-CF preconcentrator, which was shown to be 7-21%. The air flush concentrate was shown to be 7.2× to 10.4× concentrated, compared to the input sample, and the water flush concentrate was even more concentrated at approximately 21×. We also calculated the viability (defined as the live cell numbers/total cell numbers×100%, normalized to the viability of the input sample; e.g., if the input sample had a viability of 90% and the concentrate had a viability of 90%, then the viability of the concentrate was said to be 100%, as it retained all the live cells from the initial sample) of $M.$ $fujisawaense$ cells in the discharge, air flush, and water flush concentrate as shown in Table 2. Over 80% of cells were still alive after the BPE preconcentration process.

TABLE 1

Concentration ratio of $M.$ $fujisawaense$ calculated from hemocytometric and CFU count.

|  | Hemocytometric Count | | CFU Count | |
| --- | --- | --- | --- | --- |
| Discharge Ratio | 0.122 | | 0.135 | |
|  | Air Flush | Water Flush | Air Flush | Water Flush |
| Concentration Ratio | 10.4 | 21.9 | 7.2 | 21.1 |

TABLE 2

Viability of $M.$ $Fujisawaense$ cell at inlet, discharge, and concentrate outlet.

|  | Discharge | Air Flush Concentrate | Water Flush Concentrate |
| --- | --- | --- | --- |
| Viability (%) | 89.0 | 92.5 | 82.1 |

Figure 8A:
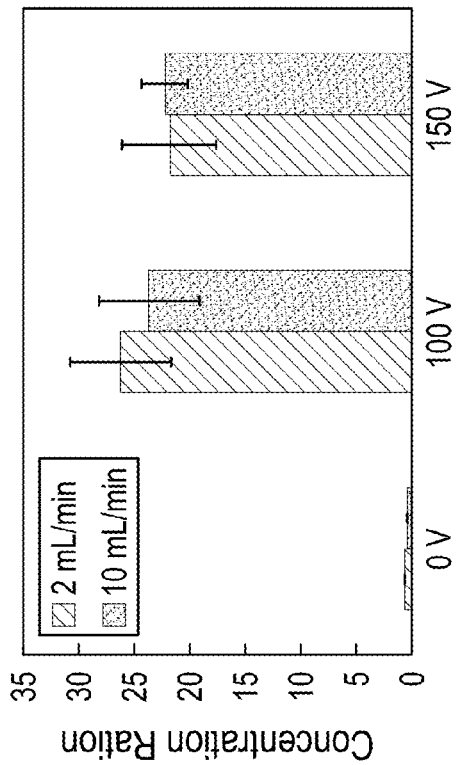
FIG. 8A includes a graph that shows the effect of voltage and flow rate on concentration ratio for the BPE preconcentration of *M. fujisawaense* with an air flush concentrate protocol.
Figure 8B:
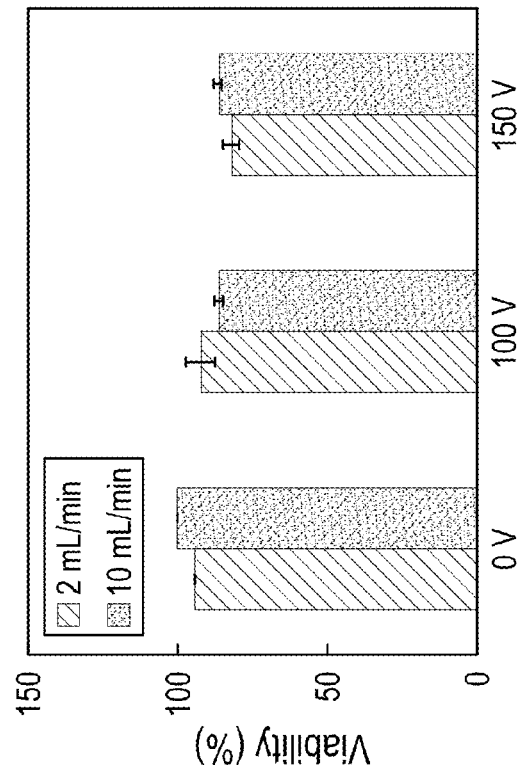
FIG. 8B includes a graph that shows the effect of voltage and flow rate on concentration ratio for the BPE preconcentration of *M. fujisawaense* with a water flush concentrate protocol.

The macrofluidic BPE preconcentrator was tested using different flow rate and voltage conditions to determine the effects of these parameters on the preconcentration ability of the device. Two different flow rates of either 2 or 10 mL/min were used, yielding operating times of 25 or five minutes, respectively, for a 50-mL sample. Three different voltages were tested: 0, 100, and 150 V. These voltages are in the range which should create the Faradaic reaction without resulting in bubble formation or other potential issues that would arise by using a higher voltage. For each parameter combination, three individual tests were undertaken to ensure statistical significance of the collected data. FIGS. 8A-8B show the $M.$ $fujisawaense$ concentration ratios of the air flush concentrate and water flush concentrate for all parameters.

A trend of worse performance at 150 V was observed, which may be attributed to the accelerated Faradaic reaction and hydrolysis at BPE under the high electric field. At 100 V, the concentrator performance was favorable when the flow rate was lower (2 mL/min) due to the stronger BPE force relative to the hydrodynamic force. Overall, a flow rate of 2 mL/min and an electrical field of 100 V showed the most promising preconcentration results. The maximum concentration ratio for the air flush and water flush concentrates were 16.8× and 26.3×, respectively, at such a condition. 100 V resulted in a stronger BPE-based preconcentration compared to 150 V. The voltage could be around 100 V (e.g., 75 or 125 V).

Figure 9A:
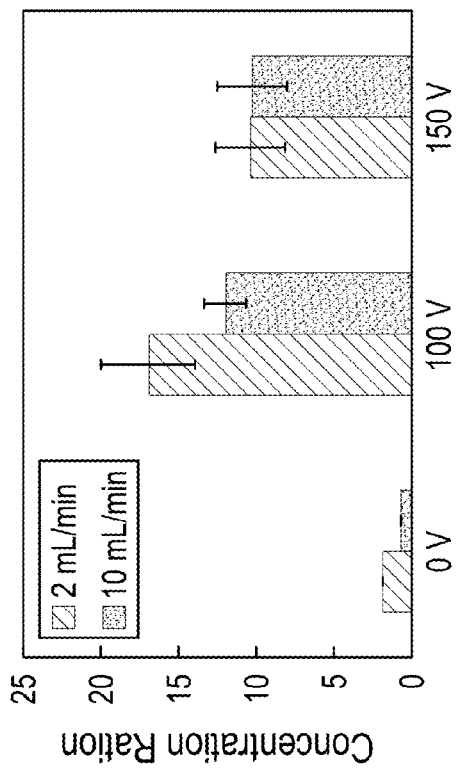
FIG. 9A includes a graph that shows the effect of voltage and flow rate on cell viability for the BPE preconcentration of *M. fujisawaense* with an air flush concentrate protocol.
Figure 9B:
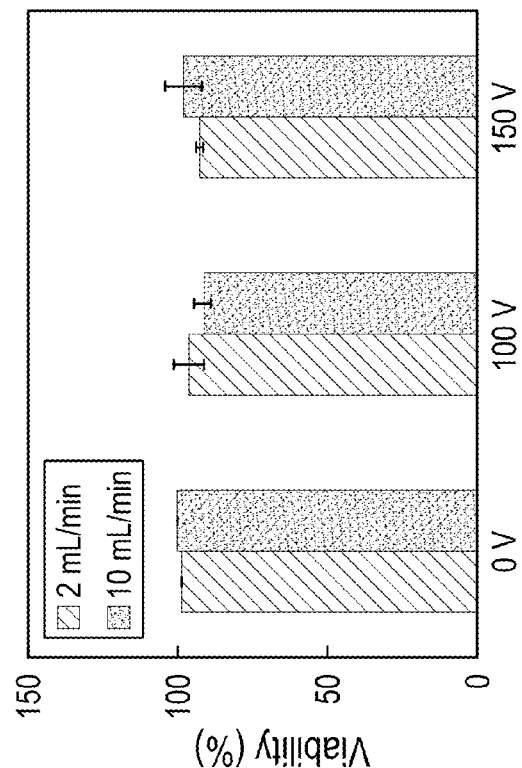
FIG. 9B includes a graph that shows the effect of voltage and flow rate on cell viability for the BPE preconcentration of *M. fujisawaense* with a water flush concentrate protocol.

FIGS. 9A-9B show the effect of flow rate and voltage on the viability of $M.$ $fujisawaense$ cells. Cell viability was calculated by taking a ratio of live to dead cells, and normalizing it by the viability of the input sample. Using this method, we showed that all the parameters resulted in a cell viability >90% for the air flush concentrate and >80% for the water flush concentrate. Because cell viability for all parameters was adequate, the optimal parameter using the device for concentrating $M.$ $fujisawaense$ in the BPE macrofluidic preconcentrator could be 2 mL/min and 100 V.

The BPE selector device can be used to perform parametric analysis to optimize the operating parameters selection by using a model with $M.$ $fujisawaense$ in the BPE preconcentrator. Experimental testing was carried out using the batch mode method, focusing on the two major parameters: (1) voltage and (2) flow rate.

Voltage and flow rate optimization was conducted with varied voltage (50-200 V) and flow rate (2 or 5 mL/min) to determine the optimal operating parameters for the BPE preconcentrator. Briefly, a large volume (50 mL) of *M. fujisawaense* sample was injected into the BPE preconcentrator at a flow rate of either 2 or 5 mL/min yielding an operating time of five or 25 min. A DC electric field (50, 75, 100, 150, 200 V) was applied to the electrodes. About 400 µL of solution was collected at the concentrate outlet during the air flush phase, followed by an additional 200 µL water flush phase and additional air.

That data (not shown) indicated the discharge (e.g., percentage of bacterial cells which escape the electric field) as a percentage of the total input for 2 and 5 mL/min. Both flow rates showed a similar trend of discharge decreasing to an optimal voltage (e.g., about 100 V for 2 mL/min, and 150 V for 5 mL/min) before increasing. The increase at a higher voltage may be attributed to the accelerated Faradaic reaction and hydrolysis at BPE under the high electric field that could potentially produce air bubbles to block the electric field. As expected, a greater number of cells escaped the electric field at 5 mL/min, compared to the slower flow rate. At 2 mL/min, 100 V, only 2% of the cells could escape the electric field, and at 5 mL/min, 150 V, 11% of cells escaped the field. Thus, the BPE preconcentrator was able to cage and retain ~98% of the bacterial cells input into the device at a flow rate of 2 mL/min and electrical potential of 100 V.

The data (not shown) indicated that the concentration ratio versus voltage followed the general trend of FIGS. 8A-8B. The data show the concentration ratio results of the air flush and water flush concentrate for both 2 and 5 mL/min. The slower flow rate resulted in a higher concentration ratio compared to the higher flow rate due to the stronger BPE force relative to the hydrodynamic force. With air flushing the concentrate, about 100 V appeared to be the maximum concentration ratio for 2 mL/min and 150 V appeared to be the maximum concentration for 5 mL/min. With water flushing the concentrate, about 75 V appeared to be the maximum concentration ratio for 2 mL/min and 175 V appeared to be the maximum concentration for 5 mL/min. However, the water flush concentrate for 5 mL/min was similar across 75 V to 200 V.

The air flush and water flush concentrate was 16.8× and 26.3× concentrated for the optimal parameter of 2 mL/min and 100 V. We were able to increase these concentration ratios to 63.2× and 32× for air and water flush concentrates, respectively, by making minor adjustments in device fabrication and assembly (i.e., enhanced device seal for minimal liquid leakage).

The data (not shown) provided the total concentration ratio (e.g., a combination of the air flush and water flush concentrates) for the various operation parameters. By evaluating the total concentration ability, along with the amount of *M. fujisawaense* present in the discharge, we found that the best voltage parameters for 2 and 5 mL/min were 100 V and 150 V, respectively. Overall, a flow rate of 2 mL/min and an electrical field of 100 V showed the most promising preconcentration results. At this optimized operating parameter, the total concentration ratio was 52.2× and the total number of cells captured by the electric field was ~98%.

Similar to the air and water flush concentrations, improvements in device assembly resulted in an increase in the total concentration ratio of *M. fujisawaense* from 20× to 52.2× at the optimal operating parameter. That is a 160% increase in the total concentration ability of the BPE preconcentrator.

It was found that the size of the target particles plays a significant role in determining electric force exerted on them within the BPE preconcentrator, and the current preconcentrator setup, which utilizes a 25-µm metallic inner mesh, did not generate an adequate force for caging and retaining the smaller *C. metallidurans* bacteria. As such, the pore size of the BPE barrier can be larger for larger particles, and smaller for smaller particles. As such, the diameter of the through-holes or apertures in the BPE barrier can be modulated to accommodate the size of substance or particle to be concentrated upstream of the BPE. The metallic mesh used to generate the bipolar electric field in the *M. fujisawaense* experiments had a weave with 25-µm gaps. In order to generate a more powerful electric force within the BPE preconcentrator that was capable of caging and retaining the smaller bacteria (like *C. metallidurans*), the current mesh was swapped out with a 5-µm mesh. Next, a field alternating test was performed using the BPE preconcentrator with the new 5-µm mesh to establish proof-of-concept of the capture/release ability of the device.

Figure 10:
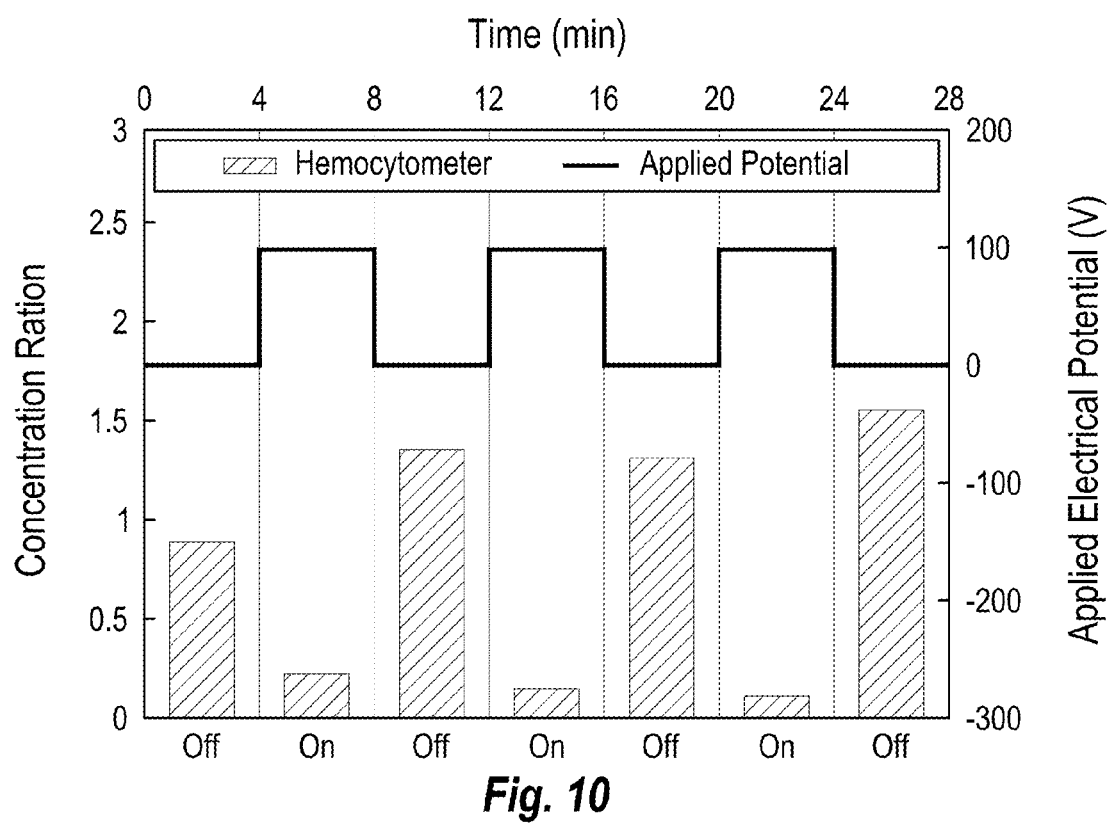
FIG. 10 includes a graph that shows the concentration ratio of the collected *C. metallidurans* at the discharge outlet with the alternating electric potential.

A field alternating test was conducted for the small 5-µm pore mesh with the smaller bacterial. In this test, we alternated the electric field between on and off for three cycles, and each cycle lasted for six minutes, i.e., the electric field was off for the time slots 0-4, 8-12, 16-20, 24-28 minutes and on (150 V) for 4-8, 12-16, 20-24 minutes. The number of *C. metallidurans* cells in the solutions collected at the discharge outlet during the "on" and "off" periods were compared to verify the effectiveness and caging capacity of the BPE exclusion zone. The sample was injected at 2 mL/min, and 8 mL was collected at the discharge outlet for each on/off period (four minutes). Samples were stained with SYTO® 9 and Propidium Iodide for visualization of bacteria and to facilitate hemocytometric counting. The number of *C. metallidurans* cells in the collections was analyzed using a hemocytometer, and their concentration ratio (i.e., concentration relative to the inlet sample concentration) was measured using hemocytometer counts as depicted in FIG. 10. It can be seen that the number of *C. metallidurans* cells collected with the electric field activation was about one order of magnitude less than that in the field-off case. The alternating tests convincingly substantiated the effectiveness of the electric field created by the 5-µm metallic mesh in terms of excluding and caging *C. metallidurans*.

Upon verification of BPE exclusion of *C. metallidurans*, next we performed preconcentration tests (e.g., including a caging phase and a flush phase) to quantify the preconcentrator performance using the 5-µm mesh. A large volume (50 mL) of the *C. metallidurans* sample was injected into the BPE preconcentrator at a flow rate of 2 mL/min yielding an operating time of 25 minutes. A DC electric field of 100 V was applied to the electrodes. About 400 µL of solution was collected at the concentrate outlet during the air flush phase, followed by an additional 200 µL water flush phase and additional air.

Hemocytometric and CFU images of the cell solution were collected at the inlet, discharge outlet, and concentrate outlet. Two different fluorescence dyes (SYTO® 9 and Propidium Iodide) were used to label the live cells and damaged cells, respectively. All the results matched very well and clearly exhibited an order-of-magnitude enrichment of the *C. metallidurans* cells in the concentrate relative to the inlet sample. Table 3 delineates the discharge ratio (defined as the concentration at the discharge outlet over the concentration at the inlet) and concentration ratio for both the air flush and water flush concentrates, calculated from different counting methods (both hemocytometric and CFU count). An average of 22-25% cells (discharge ratio range from 0.22 to 0.25 for hemocytometric and CFU, respectively) escaped via the discharge outlet. The air flush concentration ratio for the hemocytometric and CFU count was shown to be 34× and 15.4×, respectively, and the water flush concentrate was even more concentrated at approximately 43.6× and 18.5×. We also calculated the viability (defined as the live cell numbers/total cell numbers×100%, normalized to the viability of the input sample; e.g., if the input sample had a viability of 90% and the concentrate had a viability of 90%, then the viability of the concentrate is said to be 100%, as it retains all the live cells from the initial sample) of *C. metallidurans* cells in the discharge, air flush, and water flush concentrate as shown in Table 4. Over 80% of cells were still alive after the BPE preconcentration process.

TABLE 3

Concentration Ratio of *C. metallidurans* Calculated from Hemocytometric and CFU Count.

| | Hemocytometric Count | | CFU Count | |
|---|---|---|---|---|
| Discharge Ratio | 0.22 | | 0.25 | |
| | Air Flush | Water Flush | Air Flush | Water Flush |
| Concentration Ratio | 34.0 | 43.6 | 15.4 | 18.5 |

TABLE 4

Viability of *C. metallidurans* Cell at Inlet, Discharge, and Concentrate Outlet.

| | Discharge | Air Flush Concentrate | Water Flush Concentrate |
|---|---|---|---|
| Viability (%) | 97.8 | 83.2 | 85.0 |

Studies were conducted to compare mesh sizes. After establishing successful preconcentration of *C. metallidurans* using the 5-μm mesh, we compared the results of BPE preconcentration using different mesh sizes (5, 10, and 25-μm weaves) at a flow rate of 2 mL/min and electric field of 100 V, to determine the optimal mesh size. Both the 5 and 10-μm meshes resulted in a significant decrease in the percentage of *C. metallidurans* in the discharge, but the 5-μm mesh resulted in the greatest improvements in overall concentration ratio (data not shown). By utilizing a 5-μm mesh size, we were able to generate an adequate electric field to significantly decrease discharge from 55% to 26%, and increase the total concentration ratio from 10.9× to 38.5×.

The BPE preconcentrator was tested using different flow rate and voltage conditions to determine the effects of these parameters on the ability to preconcentrate *C. metallidurans*. Two different flow rates of either 2 or 5 mL/min were used, yielding operating times of 25 or 10 minutes, respectively, for a 50-mL sample. Voltages ranging from 75 to 150 V (including a 0 V parameter to demonstrate that the metallic mesh was not acting as a physical filter) were tested. These voltages were in the range which should create the Faradaic reaction without resulting in bubble formation or other potential issues that would arise by using a higher voltage. For each parameter combination, three individual tests were undertaken to ensure statistical significance of the collected data. The data (not shown) provided *C. metallidurans* concentration ratios of the air flush concentrate and water flush concentrate for all parameters. As expected, the 2-mL/min parameters performed better overall than the 5-mL/min parameters, due to a stronger BPE force relative to the hydrodynamic force. The maximum concentration ratios for the air flush and water flush concentrate, which occurred at the 2 mL/min, 75 V parameter, were 37× and 52×, respectively. However, the air and water flush concentration ratios for 75 V and 100 V were not significantly different. The 2 mL/min, 100 V parameter resulted in concentration ratios for air flush and water flush concentrate of 33.1× and 49.5×, respectively.

In order to determine if one parameter is superior to the other, we investigated the discharge ratios and total concentration ratios (a combination of air flush and water flush concentration ratios). The number of *C. metallidurans* cells in the discharge was significantly higher at the 5-mL/min flow rate compared to the 2-mL/min flow rate, as expected. The discharge percentages at 75 V and 100 V for the 2-mL/min flow rate were 25.5% and 26.8%, respectively, with no significant difference in error between them. Likewise, the total concentration ratios for these parameters were 42.0× and 38.5×, with no significant difference. Therefore, the parameter of 2 mL/min and 100 V is the optimal choice for operation of the BPE preconcentrator, as it will provide the greatest ability to cage and concentrate both *M. fujisawaense* and *C. metallidurans*. However, ranges outside this optimum can be used for 2 mL/min. The value can increase on increasing flow rate.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The following references are incorporated herein by specific reference in their entiregy: (1) Bipolar Electrode Focusing: The Effect of Current and Electric Field on Concentration Enrichment. Robbyn K. Perdue, Derek R. Laws, Dzmitry Hlushkou, Ulrich Tallarek, and Richard M. Crooks, Analytical Chemistry, 2009, 81, pp. 10149-10155; and (2) Bipolar Electrodes: A Useful Tool for Concentration, Separation, and Detection of Analytes in Microelectrochemical Systems, Robbyn K. Anand, Derek R. Laws, Kwok-Fan Chow, Byoung-Yong Chang, John A. Crooks, and Richard M. Crooks, Analytical Chemistry, 2010, 82, pp. 8766-8774.

The invention claimed is:

1. An analyte selection device, the device comprising:
   a body having at least one channel wall defining a fluid channel between a channel inlet at an inlet region and a channel outlet at an outlet region, the fluid channel having a first cross-sectional profile;
   a first electrode at the inlet region of the fluid channel;
   a second electrode at the outlet region of the fluid channel;
   a bipolar electrode (BPE) located in the fluid channel between the channel inlet and channel outlet and positioned as a barrier wall partitioning the fluid channel into the inlet region and outlet region and having the first cross-sectional profile and extending between the at least one channel wall, the BPE having a channel inlet side as a first side of the barrier wall and a channel outlet side as a second side of the barrier wall,
   the BPE being positioned across the fluid channel so as to have the channel inlet side oriented toward the inlet region and have the channel outlet side oriented toward the outlet region with a plurality of fluid passages that fluidly couple the channel inlet side of the BPE with the channel outlet side of the BPE the chamber
   the BPE partitioning the fluid channel into a concentrate portion between the first electrode and channel inlet side of the BPE and a filtrate portion between the channel outlet side of the BPE and second electrode;
   the first electrode being one of an anode or cathode electrically coupled with the channel inlet side of the BPE and the second electrode being the other of the anode or cathode electrically coupled with the channel outlet side of the BPE; and
   an electronic system operably coupled with the anode and cathode so as to polarize the BPE.

2. The device of claim 1, wherein a segment of the fluid channel is a chamber having the BPE, the chamber being fluidly coupled with the channel inlet and channel outlet and having a dimension larger than the channel inlet and channel outlet, the chamber having the concentrate portion between the channel inlet and BPE, the chamber having the filtrate portion between the BPE and channel outlet.

3. The device of claim 2, comprising one or more outlet side channels fluidly coupled with the concentrate portion of the chamber, each outlet side channel being located in the inlet region between the channel inlet and channel inlet side of the BPE.

4. The device of claim 1, comprising one or more outlet side channels fluidly coupled with the concentrate portion of the fluid channel, each outlet side channel being located in the inlet region between the channel inlet and channel inlet side of the BPE.

5. The device of claim 1, wherein the BPE is a permeable barrier BPE that extends across the fluid channel between one or more side walls of the body so as to bisect the fluid channel and provide a barrier to fluid flow, so that fluid flows through the channel inlet, through the plurality of fluid passages in the BPE, and then through the channel outlet.

6. The device of claim 1, wherein a surface of the channel inlet side of the BPE is orthogonal with a primary direction of fluid flow between the inlet region and outlet region.

7. The device of claim 1, wherein a surface of the channel inlet side of the BPE is at an angle with a primary direction of fluid flow between the inlet region and outlet region.

8. The device of claim 1, comprising a plurality of electrically coupled BPEs in series between the channel inlet and channel outlet.

9. An analyte selection device, the device comprising:
a body having at least one wall defining a fluid channel having a channel inlet at an inlet region and a primary channel outlet at an outlet region;
an electrode of a first type associated with the inlet region or outlet region;
a first outlet side channel coupled with the body at a first intersection and having a first outlet side channel opening in the fluid channel between the inlet region and outlet region;
a second outlet side channel coupled with the body and having a second outlet side channel opening in the fluid channel between the inlet region and outlet region and being located on an opposite side of the fluid channel from the first outlet side channel opening;
a first bipolar electrode (BPE) located on a wall at the first intersection of the fluid channel and the first outlet side channel, the first BPE being on a first side of the fluid channel and being a surface of at least one of the first outlet side channel or fluid channel, the first BPE positioned to partition the first outlet side channel from the fluid channel at the first intersection, the first BPE being positioned across the first outlet side channel so as to have a first fluid channel edge oriented toward the fluid channel and a first outlet side channel edge located at the first outlet side channel, wherein at least a portion of the first fluid channel edge extends into the first side of the fluid channel, the first fluid channel edge having a first angle with the fluid channel;
a first electrode of a second type associated with the first outlet side channel such that the first BPE is between the electrode of the first type and first electrode of the second type;
a second bipolar electrode (BPE) located on a wall at the second intersection of the fluid channel and the second outlet side channel, the second BPE being on a second side of the fluid channel that is opposite of the first side of the fluid channel, the second BPE being a surface of at least one of the second outlet side channel or fluid channel, the second BPE positioned to partition the second outlet side channel from the fluid channel at the second intersection, the second BPE being positioned across the second outlet side channel so as to have a second fluid channel edge oriented toward the fluid channel and a second outlet side channel edge located at the second outlet side channel, wherein at least a portion of the second fluid channel edge extends into the second side of the fluid channel, the second fluid channel edge having a second angle with the fluid channel;
a second electrode of the second type associated with the second outlet side channel such that the second BPE is between the electrode of the first type and second electrode of the second type;
the electrode of the first type being one of an anode or cathode and the first electrode and second electrode of the second type being the other of the anode or cathode; and
an electronic system operably coupled with the anode and cathode so as to polarize the pair of BPEs.

10. The device of claim 9, where the first fluid channel edge of the first BPE and second fluid channel edge of the second BPE extend into the fluid channel to have a decreasing distance therebetween from the inlet region to the outlet region.

11. The device of claim 9, where both the first BPE and second BPE each have a planar surface with respect to a direction of fluid flow in the fluid channel such that the fluid flows in a direction over the planar surface.

12. The device of claim 9, comprising a plurality of the first BPEs and first side channels and a plurality of the second BPEs and second side channels opposite of the first BPEs and first side channels between the inlet region and outlet region.

13. The device of claim 9, wherein the first BPE partitions the fluid channel from the first outlet side channel and the second BPE partitions the fluid channel from the second outlet side channel so that there is a portion of the fluid channel between the first BPE and second BPE.

14. The device of claim 9, wherein the first BPE extends into the first outlet side channel and the second BPE extends into the second outlet side channel.

15. The device of claim 9, wherein the surface of the channel inlet edge of the first BPE is oriented toward the surface of the channel inlet edge of the second BPE with the fluid channel therebetween.

* * * * *